(12) United States Patent
Hashimshony et al.

(10) Patent No.: US 7,082,325 B2
(45) Date of Patent: Jul. 25, 2006

(54) METHOD AND APPARATUS FOR EXAMINING A SUBSTANCE, PARTICULARLY TISSUE, TO CHARACTERIZE ITS TYPE

(75) Inventors: Dan Hashimshony, Givat Ada (IL); Gil Cohen, Jersusalem (IL)

(73) Assignee: Dune Medical Devices Ltd., Caesaria (IL)

( * ) Notice: Subject to any disclaimer, the term of this patent is extended or adjusted under 35 U.S.C. 154(b) by 4 days.

(21) Appl. No.: 10/891,750

(22) Filed: Jul. 15, 2004

(65) Prior Publication Data

US 2005/0021019 A1    Jan. 27, 2005

Related U.S. Application Data

(60) Provisional application No. 60/481,130, filed on Jul. 24, 2003.

(51) Int. Cl.
*A61B 5/055* (2006.01)
(52) U.S. Cl. .................. 600/411; 600/421; 600/547
(58) Field of Classification Search .............. 600/411, 600/421–423, 547
See application file for complete search history.

(56) References Cited

U.S. PATENT DOCUMENTS

| | | | | |
|---|---|---|---|---|
| 4,625,171 A | * | 11/1986 | Sekihara et al. | 324/312 |
| 4,689,567 A | * | 8/1987 | Maudsley | 324/309 |
| 4,751,464 A | * | 6/1988 | Bridges | 324/318 |
| 5,442,290 A | * | 8/1995 | Crooks | 324/309 |
| 5,735,278 A | * | 4/1998 | Hoult et al. | 600/422 |
| 5,758,646 A | * | 6/1998 | Van Der Meulen et al. | 600/407 |
| 6,397,095 B1 | * | 5/2002 | Eyuboglu et al. | 600/411 |
| 6,766,185 B1 | * | 7/2004 | Scott | 600/410 |
| 2001/0051774 A1 | * | 12/2001 | Littrup et al. | 600/547 |
| 2003/0199753 A1 | * | 10/2003 | Hibner et al. | 600/411 |

FOREIGN PATENT DOCUMENTS

WOPCT WO 2005/009200    3/2005

OTHER PUBLICATIONS

Smith et al. "In Vivo Measurement of Tumor Conductiveness With the Magnetic Bioimpedance Method", IEEE Transactions on Biomedical Engineering, 47(10): 1403-1405, 2000.
Schwan "Mechanism Responsible for Electrical Properties of Tissues and Cell Suspensions", Medical Process Through Technology, 19: 163-165, 1993.
Surowiec et al. "Dielectric Properties of Breast Carcinoma and the Surrounding Tissues", IEEE Transactions on Biomedical Engineering, 35(4): 257-263, 1988.

* cited by examiner

*Primary Examiner*—Brian L. Casler
*Assistant Examiner*—Julianne M Sullivan

(57) ABSTRACT

A method and apparatus for examining a substance volume to characterize its type, particularly useful for examining tissue to characterize it as cancerous or non-cancerous. The method comprises: applying a polarizing magnetic field through the examined substance; applying RF pulses locally to the examined substance volume such as to invoke electrical impedance (EI) responses signals corresponding to the electrical impedance of the substance, and magnetic resonance (MR) responses signals corresponding to the MR properties of the substance; detecting the EI and MR response signals; and utilizing the detected response signals for characterizing the examined substance volume type.

51 Claims, 15 Drawing Sheets

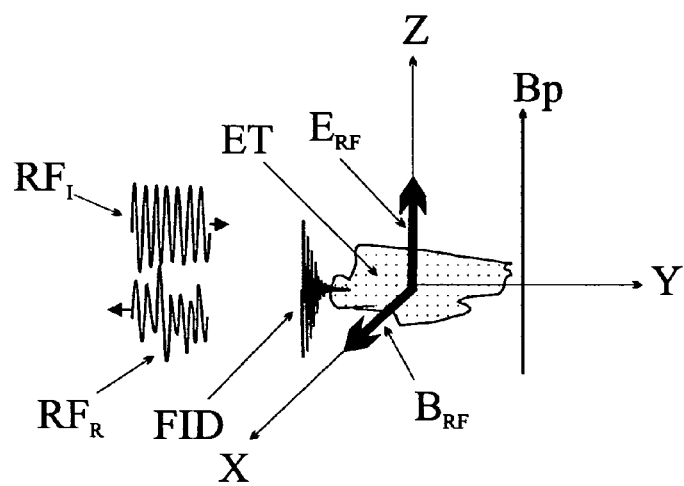
FIG. 1
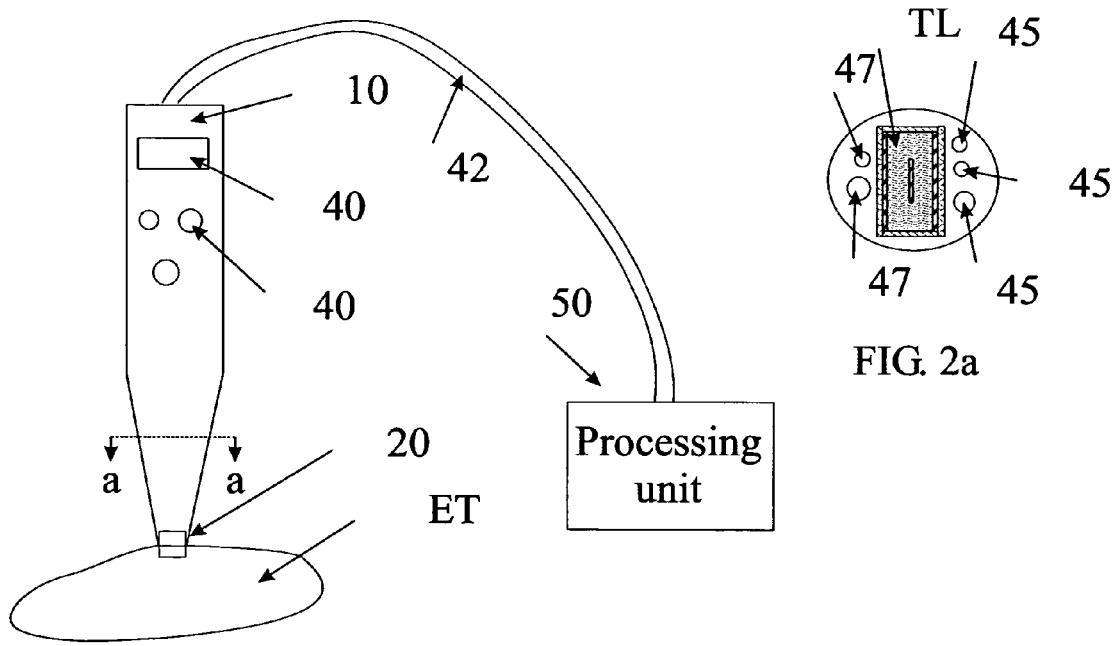
FIG. 2
FIG. 2a

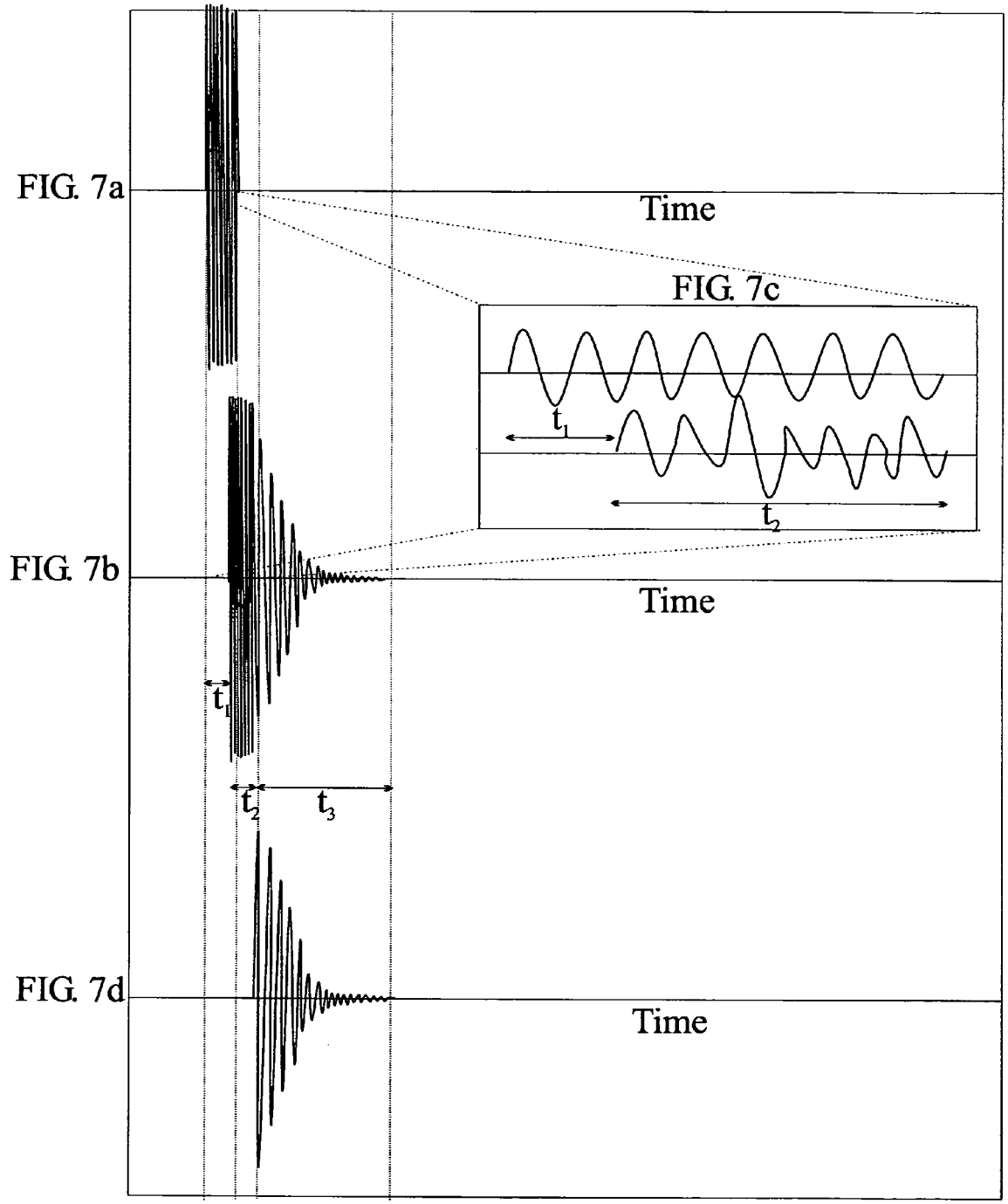

METHOD AND APPARATUS FOR EXAMINING A SUBSTANCE, PARTICULARLY TISSUE, TO CHARACTERIZE ITS TYPE

RELATED APPLICATIONS

This application claims priority from U.S. Provisional Patent Application No. 60/481,130, filed Jul. 24, 2003, which is incorporated by reference as if fully set forth herein.

FIELD AND BACKGROUND OF THE INVENTION

The present invention relates to a method and apparatus for examining a substance to characterize its type and composition. The invention is particularly useful for examining tissue in order to characterize it as cancerous or non-cancerous, and the invention is therefore described below with respect to this application.

Today, in many surgical applications there is a need to cut biological tissues of a specific type while avoiding cutting tissues of other types. For example, in a tumor removal surgery, the surgeon attempts to cut around the tumor in order to remove it. There are many ways to perform this medical procedure but all share the same fundamental principle: Never cut through a tumor. This principle is the core of good practice and markedly affects the success rate of tumor removal procedures. Failing to keep this fundamental rule increases the failure rate of the surgery, the reoccurrence rate of the cancer, and the rate of necessary re-excisions.

Nevertheless, during surgery the surgeon does not have (except for his trained eyes and fingers) any real-time indication of the kind of tissue that is being cut. Furthermore, if the surgeon cuts through healthy tissue and then, accidentally, cuts a small portion of a malignant tissue, this will be noticed, if at all, only in the pathologist report after conducting a biopsy. Therefore, from the point of view of organ conservation and reoccurrence rate reduction, it is highly desirable to use a real time tool that displays the type of tissue being cut and alerts the surgeon whenever a tumor is about to be cut.

In many medical procedures, the diagnostics tool and surgical assist tools are serially applied to the patient in order to increase the specificity and sensitivity of the tests. When trying to perform such serial examinations during surgical operations, the problem of coordinate registration becomes a crucial one. Therefore, a tool that enables simultaneous measurement of multiple, independent tissue characterization modalities in the same place (i.e. of the same biological mass) possess an added and synergetic value.

There are numerous modalities, methods and devices that have been developed in order to differentiate and characterize tissue as being malignant or healthy. Still, use of multi-modality tissue sensing and characterization probes, as described, for example, in U.S. Pat. No. 6,109,270 and U.S. Pat. No. 20030045798, has the possibility of enhancing the differentiation capabilities of the device.

The ability of detect cancer cells, and especially breast cancer, using electric impedance of tissue is well established in the biomedical literature[1,2,3,4]. Another technique, based on magnetic bioimpedance[5], measures the bioimpedance by magnetic induction. Although the exact mechanism responsible for tissue impedance at various frequencies is not completely understood, the general mechanism[6,7] is well explained by semi-empirical models that are supported by experiments[8,9,10].

Variations in electrical impedance of the human tissue are used in, for example U.S. Pat. No. 4,291,708 and U.S. Pat. No. 4,458,694, to provide indications of tumors, lesions and other abnormalities. Millimeter and microwave devices are used, for example in U.S. Pat. No. 5,807,257, U.S. Pat. No. 5,704,355 and U.S. Pat. No. 6,061,589, to measure bio-impedance and to detect abnormal tissue. In U.S. Pat. No. 20030187366 (by the same assignee as the current application) is disclosed a method and apparatus for locally characterizing tissue by its Electric Impedance properties.

MRI has long been recognized as a useful modality/method for tissue characterization as malignant or healthy. MRI is "global" method, which requires positioning of the patient within the apparatus, and is therefore not suitable for use during an operation procedure. Variations of the MRI modality which provide a local MRI probe have been disclosed, for example, in U.S. Pat. No. 5,572,132 where a MRI response is detected in an intravascular device, in WO0239132 where a variation of the intravascular approach is presented, and in U.S. Pat. No. 6,489,767, where a local MRI surface characterization method is disclosed.

Motion is another problem in any real time imaging or detection tool, such as Magnetic Resonance Imaging (MRI), that demands stationary objects for good imaging results. For example, during breast surgery, the movement of the breast with breathing is a major problem for achieving good resolution. An in situ miniature real-time tool that moves with the body avoids the motion problem. When such a detection tool also possesses an in-situ marking capability, the problem of coordinate registration is substantially eliminated.

OBJECTS AND BRIEF SUMMARY OF THE PRESENT INVENTION

A broad object of the present invention is to provide a method and apparatus having advantages in one or more of the above respects for examining a substance in order to characterize the type of the substance. A more particular object of the present invention is to provide a method and apparatus especially useful in examining tissue in order to characterize the examined tissue as being cancerous, or non-cancerous, or partially cancerous. Partially cancerous meaning that the examined tissue volume contains both cancerous and non-cancerous tissue.

According to one aspect of the present invention, there is provided a method of examining a substance volume to characterize its type, comprising:

applying locally a polarizing magnetic field through the examined substance volume:

applying RF pulses locally to the examined substance volume such as to invoke electrical response signals corresponding to the electrical impedance (EI) of the examined substance volume, and magnetic resonance (MR) response signals corresponding to the MR properties of the examined substance volume;

detecting locally the EI and MR response signals;

and utilizing the detected response signals for characterizing the type of substance in the examined substance volume.

According to a further feature in the described preferred embodiments, the polarizing magnetic field is varied such as to vary the EI response signals and MR response signals invoked from the examined substance volume, the variations in the response signals also being detected and utilized for characterizing the substance type.

The present invention is thus based on the multi-modality sensing approach, namely on multi-modality sensing and detection of electric impedance (EI) and magnetic resonance (MR) properties. Preferably, the sensors are integrated into one sensor head, and the modalities are synergistically combined so that a third modality is produced. The method thus utilizes the simultaneous measurement of EI properties of a specific region of the examined tissue (or other substance), combined with the measurement of MR properties of the same region of tissue. The third synergetic mode if utilized, relies on the induced change in the EI properties due to the MR absorption of the incident electromagnetic radiation pulse.

The MR response of the tissue probed can result from two general types/classes of microscopic spins: electronic and nuclear. Electronic spins are from paramagnetic species/molecules/atoms having a non-zero spin due to their electron configuration. This type of response is know in the literature as Electron Magnetic Resonance (EMR), or Electron Spin Resonance (ESR), or Electron Paramagnetic Resonance (EPR). Nuclear spins are from atoms with a non-zero nuclear magnetic moment. This type of response is know in the literature as Nuclear Magnetic Resonance (NMR).

The various MR responses thus include: NMR; EMR, also known as EPR or ESR; Proton Electron Double Resonance (PEDR), also known as Overhauser MR; Longitudinally-detected ESR (LODESR); Field-cycled PEDR (FC-PEDR); and others familiar to those skilled in the art. Various methods are known for detecting these MR responses.

The preferred mode of the invention described below involves detecting NMR properties, more particularly the simultaneous (i.e., within a few seconds) measurement of EI properties of a specific region (voxel) of tissue (or other substance), combined with the measurement of NMR properties from that same voxel. The third synergetic mode, namely the measurement of the induced changes in the EI properties due to the application of the magnetic field for measuring the NMR properties, is preferably also effected in order to enhance the results achievable by the EI and NMR measurements.

While the NMR process is preferred, and is particularly referred to in the description below, the invention may also be implemented by detecting other types of MR properties particularly EMR properties, and with other means for detecting MR responses. However, there are some important differences between the NMR and EMR processes, including the following:

1. EMR probes completely different tissue parameters/states than NMR probes, including metabolism rates, pH, NO concentration, free radicals, reactive oxygen species, and oxygenation state.
2. EMR is usually preformed in conjugation with contrasting agents. These are spin-trap molecules that stabilize the paramagnetic species.
3. The polarizing magnetic fields used in EMR are much lower than those used in NMR.

Since the described probe can work up to a few Ghz (at least 5 Ghz), it can be used both as an EMR probe and as an NMR probe.

The term "examined substance volume", as used herein, refers to the volume/part of the substance which is examined for (1) electrical impedance (EI) response properties, and (2) magnetic resonance (MR) response properties during one measurement process. This examined substance volume is in the range of about 0.2 mm$^3$ to 8000 mm$^3$. The total examined substance generally consists of many examined substance volumes. The examined substance volume is sometimes also referred to (especially in the magnetic resonance imaging community) as a "voxul".

The term "locally" as used herein, refers to the fact that the polarizing magnetic and electromagnetic fields are applied only to the examined substance volume and its immediate surroundings (no more than about five time the largest dimension of the examined substance volume). Thus, only a negligible amount of the polarizing magnetic and electromagnetic fields are present beyond the immediate surroundings of the examined substance volume, as distinguished from, for example, conventional magnetic resonance imaging (MRI) where both the polarizing fields and the RF pulses are applied to the complete body being imaged.

According to still further features in the described preferred embodiments, the detected EI response signals invoked by the RF pulses are processed to calculate the effective electrical impedance of the examined substance, which calculated electrical impedance is utilized in characterizing the substance type. In addition, the RF pulses invoke MR free induction decay (FID) signals, corresponding to the echos from excited spins in the examined substance when returning to equilibrium, which FID signals are also detected and utilized in characterizing the substance type.

In one preferred embodiment of the invention described below the RF pulses are applied locally via a transmission line in contact with one side of the examined substance, the RF pulses invoking reflected pulses which are detected and utilized in characterizing the substance type. In another described preferred embodiment, the RF pulses are applied locally via a first transmission line which is brought into contact with one side of the examined substance, while a second transmission line is brought into contact with the opposite side of the examined substance, the RF pulses from the first transmission line being transmitted through the examined substance, detected by the second transmission line, and utilized in characterizing the substance type.

According to still further features in the described preferred embodiments, the detected response signals are utilized to characterize the substance type by: analyzing the detected response signals for predetermined parameters characterizing the substance type; and comparing the predetermined parameters with corresponding parameters of known substance types to produce a best match. Preferably, the RF pulses are applied as a sequence of pulses in which some pulses are optimized for EI measurements, and others are optimized for MR measurements.

The detected MR response signals may be analyzed for, for example: spin density, longitudinal relaxation time (T1), and/or transverse relaxation time (T2) of the examined substance.

Preferably, and according to further features in the described preferred embodiments, the detecting of the EI and MR response signals includes: (a) collecting the EI response signals and the MR response signals; (b) analyzing the collected response signals for predetermined parameters characterizing the substance type; (c) modeling the signal parameters into a set of parameters; and (d) classifying the set of parameters according to known parameter sets of known substance types.

According to another aspect of the present invention, there is provided apparatus for examining a substance to characterize its type, comprising: magnetic means for applying locally a polarizing magnetic field through the examined substance volume; and an electrical control and processing system for: (a) applying RF pulses. locally to the examined substance volume such as to invoke electrical impedance (EI) response signals corresponding to the electrical impedance of the substance, and magnetic resonance (MR) response signals corresponding to the MR properties of the examined substance volume; (b) detecting the EI and MR response signals; (c) and utilizing the detected response signals for characterizing the substance type.

As indicated earlier, the novel method and apparatus are particularly useful for examining tissue to characterize it as cancerous, or non-cancerous tissue, or partially cancerous tissue.

The advantages achievable by the invention could be further enhanced by adding even more modalities to the EI sensor, by using other, not co-excited modalities, or by combining EI and MR (e.g., NMR) with mechanical and ultrasound impulses. The detection is based on statistical analysis algorithms that compare the measured properties of the tissue investigated to known tissue type properties.

The apparatus may thus be implemented in an external mother unit and a handheld probe connected to it via a flexible transmission line. The hand held probe would include the integrated sensor head, handgrip, and some user controls and indicators.

The invention may be used at the operation table by the surgeon. During an operation, the surgeon would contact the sensor head of the probe with suspicious tissue and receive an immediate indication, based on both electric EI properties and MR properties, whether the contact tissue is cancerous or non-cancerous. Such device could indicate the presence of malignant clusters of cells in the near region (up to about 5–12 mm) from the surface, into the depth of the tissue. This indication would allow the surgeon to achieve the desired clean margin. The device could also include a marking capability that physically marks the tissue at the examination point with the detection results. The simplicity of such an embodiment of the invention would enable its use in a wide variety of tools, especially for tissue recognition during surgical operations.

The apparatus may also be used by the surgeon to perform a scan of the excised section on the operating table, immediately after the section has been removed from the patient's body.

According to other possible embodiments, the probe may also be mounted on a needle to be inserted into the patient's body to perform a biopsy, and to examine the tissue sample, and/or to guide the movement of the biopsy needle during the biopsy procedure. The guiding instructions may be used to assist in the localization of the biopsy needle, and thereby, to prevent the well-known "miss localization of the biopsy site" mistake.

According to yet other embodiments, the probe may also be used in conjunction with a cutting blade or ablation device to perform a real time detection of cancerous tissue followed by immediate local excision.

The probe may also be mounted on the distal tip of a catheter, for example a coronary artery catheter, to be used to identify the tissue and to identify changes in the tissue near the vicinity of the probe. The latter can be very helpful in the case of plaque detection, especially vulnerable plaque, for in-stent re-stenosis inspection, or for general coronary artery inspection.

Another advantage of the presented method is that it can be easily implemented in the form of a single-sided probe, which allows approaching the suspicious tissue from one side only, as is frequently the case during surgical procedures.

In the described preferred embodiments the detection algorithm is based on statistical analysis of the measured parameters, and on identification of similarities between the set of measured parameters and sets of pre-recorded parameters of known tissue types stored in the memory bank of the system. The measured parameters from all modalities are mathematically transformed to an independent parameter set. Thus, by combining information from the different independent modalities of EI and MR, the base for comparison is wider than when using just only one modality. As a result, the probe is capable of providing the surgeon information with superior reliability regarding the type (e.g., cancerous or non-cancerous) of the probed tissue.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a diagram illustrating the basic principle of operation involved in the described preferred embodiment of the present invention, and particularly illustrating the RF pulses thereof applied to the examined tissue, the polarizing magnetic field through the examined tissue, and the EI and MR (preferably NMR) response signals invoked by the examined tissue;

FIG. 2 is a block diagram illustrating one form of apparatus constructed in accordance with the present invention;

FIG. 2a is a sectional view of FIG. 2 along line a—a;

FIGS. 7a–7d are waveforms helpful in understanding the operation of the apparatus of FIGS. 2–6;

Figure 3:
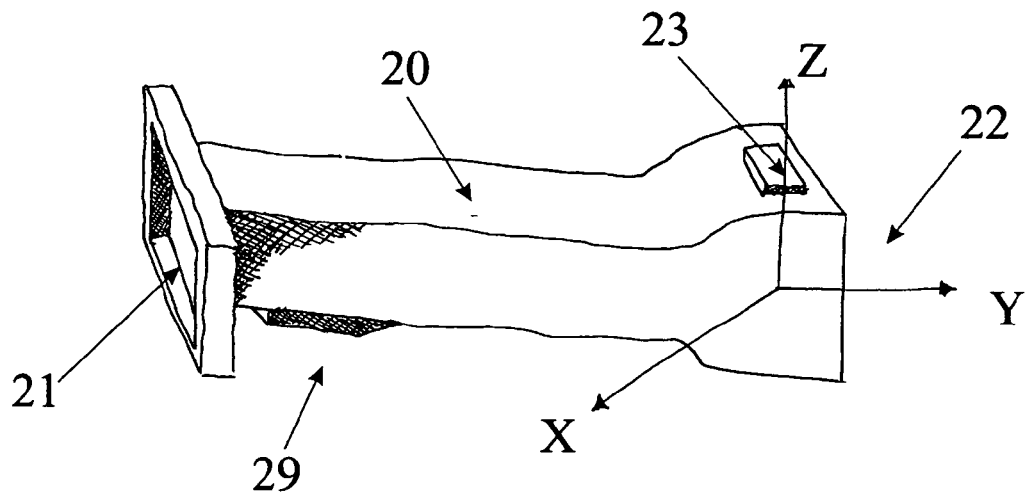
FIG. 3 is a three-dimensional view illustrating the sensor head in the apparatus of FIG. 2.

It is to be understood that the foregoing drawings, and the description below, are provided primarily for purposes of facilitating understanding of the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS OF THE INVENTION

Basic Principle of Operation (FIG. 1)

The basic way by which the present invention realizes the multi-modality approach is by combining EI sensing and NMR sensing into one integrated sensor head that collects signals corresponding to both phenomena substantially simultaneously (i.e., within a short, e.g., up to a few seconds) from the same tissue volume (the examined tissue volume). Using the combined modalities sensor, a calculation of the dielectric properties of the examined tissue volume can be derived, as well as the nuclear magnetic resonance properties, known as NMR. Furthermore, the change in the dielectric properties of the examined tissue volume induced by the presence of the nuclear spin polarizing magnetic field is also measured, forming a third modality. Tissue characterization or recognition is performed by using algorithms based on statistical analysis of the measured parameters, and by identifying similarities between the set of measured parameters and sets of pre-recorded parameters of known tissue types stored in the memory bank of the system.

The principle of operation can be briefly described by the following operations: application of a constant, or slowly varying polarizing magnetic field to a tissue volume; application of RF electromagnetic fields (while the polarizing magnetic field is applied) to the same tissue volume; and detection of both the EI response and MR (preferably NMR) signals from that tissue volume.

The geometry (direction) of the generated polarizing magnetic field must be such that it always has a component perpendicular (orthogonal) to the magnetic field associated with the RF radiation generated in the vicinity of the probe. In the preferred realization, the polarizing field always has a component in the direction of the electric field associated with the RF radiation generated in the vicinity of the probe.

FIG. 1 is a schematic illustration of the presented geometry. As illustrated, the tissue volume examined ET is incident by the RF radiation pulse $RF_I$ generated by the source and transmitted by the transmission line (TL, FIG. 2a), with that radiation reflected back as a reflected pulse $RF_R$. When The E-field component $E_{RF}$ of the incident pulse $RF_I$ is in the Z direction, the B-field (magnetic) component $B_{RF}$ of the incident pulse $RF_I$ is in the direction of the X-axis. Being so, the magnetic field associated with the RF radiation generated by $RF_I$ in the vicinity of the probe induces a precession of the spins polarized by the external (polarizing) magnetic field Bp, thus generating an NMR Free Induction Decay (FID) signal FID when these spins' direction (the magnetization vector) relaxes back to the polarizing field's direction (the Z-direction in FIG. 1), following the RF pulse $RF_I$. This NMR signal is further detected simultaneously with the RF reflection response $RF_R$ of the tissue examined. The NMR signal could be detected as an absorption in the reflected spectrum of the RF signal $RF_R$, followed by the FID signal, in the X-direction in FIG. 1.

The NMR signal could also be detected by an additional magnetic transient field detector, which is perpendicular both to the polarizing magnetic field and the RF excitation related magnetic field so that it is sensitive to magnetic fields in the Y-direction in FIG. 1.

The RF signals $RF_I$ generated at the end of the transmission line TL can be used according to two modes of operation:

In a first mode of operation, they can be used with pulse duration signals which are much shorter than the time scales related to NMR signals (the spin-lattice relaxation time T1, and the spin-spin relaxation time T2), and which have a repetition rate much higher than the time scales related to NMR signals. In this case the system is viewed as a "continuous wave" NMR system, in the sense that the pumping is effectively continuous, even though the RF radiation, being extremely broadband, will have only a small bandwidth in resonance with the spins.

In a second mode of operation, the incident RF signals $RF_I$ can be pulses of a length and duty cycle comparable to those used in NMR studies, in which case the system can be viewed as a pulsed NMR system. The relaxation signals are then detected by the TL and/or an additional receiver. This second form of use is the one illustrated in FIG. 1.

For all modes of operation described above, the NMR signal generated could be of the numerous and assorted types of NMR signal known to those skilled in the art. For example, the proton density weighted (PD), the T1 weighted, and the T2 weighted, routinely used in MRI as described for example in Nitz et al "Contrast Mechanisms in MR Imaging", Eur Radiol, 9, 1032–1046 (1999).

The polarizing magnetic field can be modified, and turned on and off, thereby providing a means of measuring the dielectric response of the tissue with various types (including none) of its NMR response. By comparing these responses, the synergistic effect of the modalities is achieved, providing the additional, third modality. The ability to control the polarizing field can also be used to improve dramatically the signal-to noise ratio S/N by using phase locking techniques, by applying a modulation to the polarizing field, for example at 120 Hz. As described more particularly below, this can be achieved, for example, by moving a set of permanent magnets along the Y-direction in FIG. 1, or by changing the location or the driving current in coils, with and without a paramagnetic core. The measurement of the RF reflection is then "locked-on" to this reference frequency and phase.

The TL probe can be of various shapes and types depending on how deep the RF radiation needs to penetrate into the examined tissue. Open cavity ending, open ended, or short ended TL types of ending can be used for generating RF fields only in the near vicinity of the TL, whereupon the range of penetration would be in the order of the diameter of the TL (for coax) or the distance between the strip (for flat lines). Wideband antennas, like a conical antenna, can be used to radiate the energy into the body. The material of which the TL section attached to the permanent magnets should be magnetically transparent.

Generally speaking, the reflection depends on the impedance differences between the continuous section of the TL and its endings. As the ending could be of various types and shapes, its impedance will be correspondingly altered when placed in the close vicinity of the tissue, due to the dielectric properties of the tissue. Accordingly, the reflected pulse carries with it information about the dielectric properties of the examined tissue. These properties produce a change in the time-domain-profile of the reflected pulse. The basic measurement concept is well known and is referred to in the literature on the open-ended transmission line measurement method. A preferred construction is described in International Publication No. WO 03/060462 A2, published Jul. 24, 2003, assigned to the assignee of the present application, the contents of which are incorporated by reference.

The electrical characteristics of the reflected electrical pulse are compared, both in time domain and frequency domain, with those of the applied (incident) electrical pulse by sampling both electrical pulses at a plurality of spaced time intervals, e.g., every 0.2 nanoseconds, and comparing the voltage magnitudes of the two electrical pulses at the spaced time intervals. The reflection coefficient and the time domain filtering properties of the examined tissue are then calculated. The frequency dependent complex impedance of the tissue is then calculated using the theoretical relation between impedance and reflection. The signals are then modeled and reduced into a parameter set that describes and characterizes the tissue measured.

The EI measurement can also be conducted in the transmission mode. In this mode of operation, an electrical signal is launched via the transmission line of one probe through the examined tissue and collected by another similar open-ended probe placed on the other side of the tissue. This mode of operation has an advantage from the signal-processing standpoint (although requiring two sided approach and two probes) since the affect of the electrical properties of the tissue on the transmitted signal is stronger then on the reflected signal. This provides a better S/N for the measurement of the tissue properties. This mode of operation is more particularly described below with respect to FIG. 12.

The effect of the polarizing magnetic field on the evoked (e.g., reflected) pulses is through the additional absorption of energy from the incident pulse, by the nuclear magnetization vector created due to the presence of the polarizing field. This energy is used to create the precession of the magnetization vector around the direction of the polarizing field. This additional absorption affects the way the electric field is built inside the tissue volume and therefore changes its RF impedance EI. This absorption will appear as a change in the spectrum of the evoked pulse.

A Preferred Construction (FIGS. 2–7)

FIG. 2 illustrated one form of apparatus, therein generally designated 2, constructed in accordance with the present invention for examining tissue, indicated at ET, to characterize its type, particularly to distinguish cancerous tissue from non-cancerous tissue.

The apparatus illustrated in FIG. 2 includes a multi-modality probe 10 having a sensor head 20 to be placed into contact with the tissue ET to be examined for applying RF pulses via a transmission line TL, and sensor head 20 at the distal end of the transmission line, to the examined tissue. The applied RF pulses are such as to invoke electrical impedance (ED) response signals corresponding to the electrical impedance properties of the examined tissue, and nuclear magnetic resonance (NMR) response signals corresponding to the NMR properties of the examined tissue. Probe 10 is incorporated in a housing which is conveniently graspable by the user for manipulating the sensor head 20.

It includes the various controls and indicators, generally designated 40, used to optimize the sensor head 20 performance when applying the RF pulses to the examined tissue ET, and also when detecting the signals evoked from the examined tissue in response to the applied RF pulses. The detected signals are fed to a remotely-located processing unit 50 communicating with the probe unit 10 via a flexible cable set 42, containing the transmission line, additional signal cables and control line cables. Additional signal and control lines 45 (FIG. 2a) and utility lines 47 are also extended through the probe unit 10 up to the sensor head 20.

The probe sensing head 20 in this example is designed to detect both EI reflection signals $RF_R$ and NMR signals FID from the tissue ET. Sensing head 20 integrates both modalities and also allows the third synergetic mode to be used. Both types of signals are useful for the identification of various tissue types, such as (but not limited to) normal and cancerous tissue. The measurements are preferably performed in real-time and continuously as the probe is scanned over a tissue section, but may also be performed on the user's demand. The connection between the probe sensing head 20 and the transmission line TL is made as continuous as possible so that the probe sensing head 20 constitutes the distal end of the transmission line TL.

FIG. 3 illustrates the construction of the probe sensing head 20 and identifies the various axes involved during the operation of the probe as described more particularly below. The proximal end of sensing head 20 includes a connector 21 for connecting it to the transmission line TL so as to constitute the distal end of the transmission line. The distal end 22 of sensing head 20 is adapted to be brought into contact with the tissue to be examined. Also shown in FIG. 3 is a tuning circuit 23 for varying the impedance of the open end of the transmission line defined by the sensing head 20 at the distal end of the transmission line TL.

As indicated above, sensing head 20 constitutes the open end of the transmission line TL. It serves as both a transmitter of the RF pulses applied to the examined tissue ET when contacting same, as well as a receiver of the response signals (reflected pulses in this case) from the examined tissue. The construction of the open end of sensing head 20 is more particularly illustrated in the sectional views of FIG. 3a (the ZY-plane) and FIG. 3b (the XZ-plane).

Figure 3A:
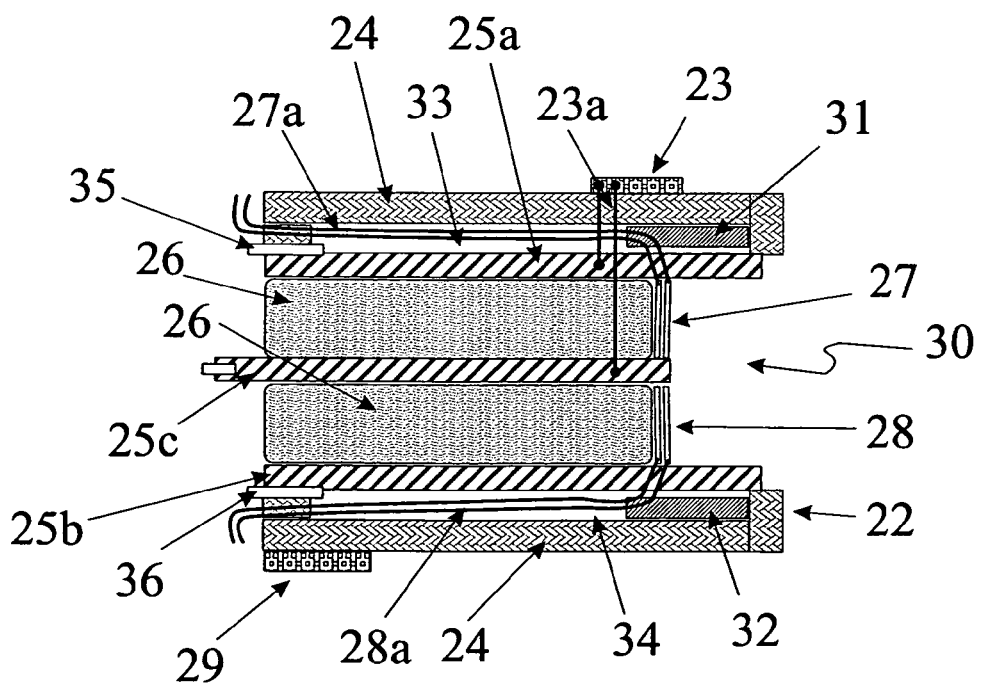
FIG. 3a and 3b are sectional views of the sensor head in FIG. 3, along the ZY-plane and XZ-plane, respectively, FIG. 4 diagrammatically illustrates the configuration of the electric and magnetic fields produced by the sensor head of FIG. 3.
Figure 3B:
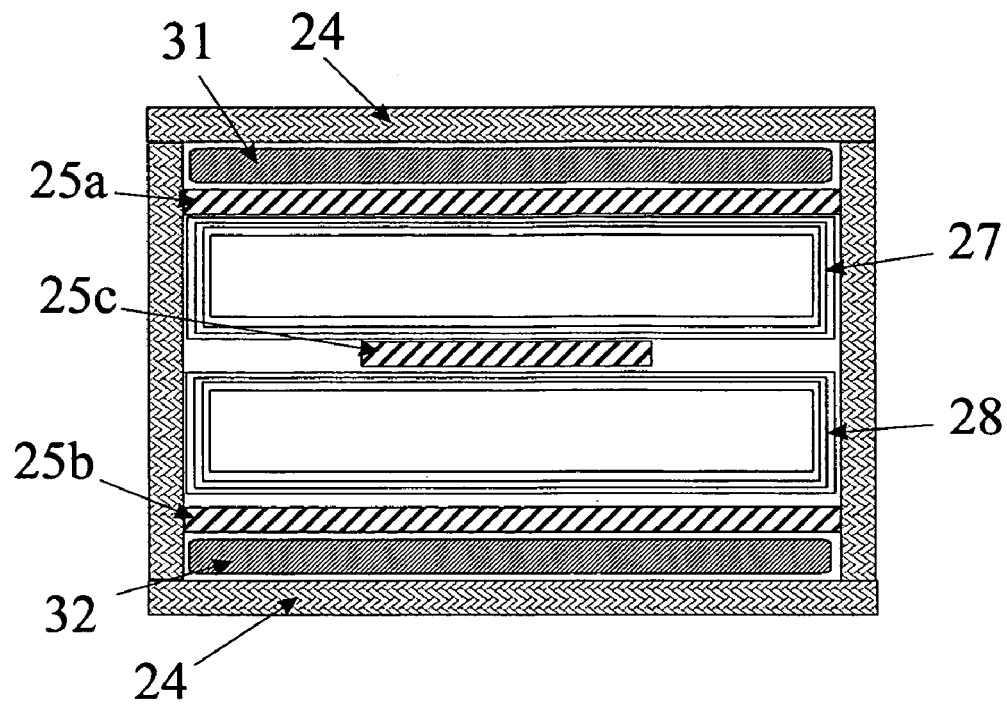

As shown in FIG. 3a, sensing head 20 includes an outer housing 24 containing a transmission line section of the strip-line type, including three conductive strips 25a, 25b, 25c, separated from each other by insulation 26. The two outer conductive strips 25a, 25b constitute the two ground plates of the strip-line, whereas the inner conductive strip 25c constitutes the inner conductor of the strip-line. The ground plates 25a, 25b are made from a magnetically transparent conductive material, e.g., aluminum.

The transmission line defined by sensing head 20 is left open-ended and serves both as a transmitter and a receiver. The open end is connected by wires 23a to the tuning circuit 23. Thus, the impedance of the open ended transmission line can be varied by tuning circuit 23 from zero up to about the open-end impedance. This tuning can be used to increase/decrease the open-ended reflectivity, and to increase/decrease the strength of the B-RF field, that is, the magnetic field generated by the transmission of the RF pulse to the sensing head 20 at the distal end of the transmission line.

As described, for example, in the above-cited International Publication No. WO 03/060462, the outer conductors 25a, 25b and the inner conductor 25c define open cavities closed by the tissue ET being examined, such that when a pulse is transmitted through the transmission line, the pulse is reflected back to the transmission line. The reflection depends on the impedance of the region at the open cavity of the probe, which impedance depends on the dielectric properties of the examined tissue closing the open of the cavity. Accordingly, the reflected pulse carries with it information about the dielectric properties of the examined tissue. These properties produce a change in the time-domain-profile of the reflected pulse.

The transmission line defined by conductors 25a–25c of the sensing head 20 also detect NMR signals evoked in response to the transmitted RF pulses. In the construction illustrated in FIG. 3a, additional NMR signals are detected by a pair of RF coils 27, 28, at the open end of the transmission line defined by conductors 25a–25c, and are outputted from the sensing head 20 via conductors 27a, 28a, respectively extending through the sensing head. The sensing head further includes a small pre-amplifier 29 which serves, together with the tuning circuit 23, in order to improve and to amplify the signals detected by the RF coils 27, 28.

Figure 4:
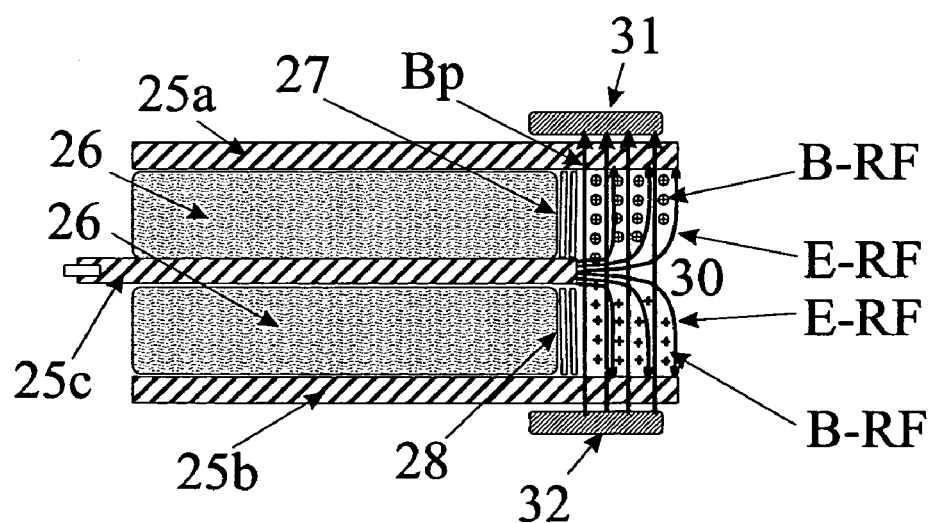

At the distal end of the probe, are positioned a pair of permanent magnets 31, 32 for generating a polarizing magnetic field Bp for aligning the spins of the nuclei in the examined tissue from which NMR signals will be generated. Magnets 31, 32 are designed to generate in region 30 a magnetic field Bp whose major component would be in the direction Z, perpendicular to the B-RF field generated in and near the open cavity. As seen in FIG. 4 the B-RF field has a different direction in the upper section of the sensor head, above the inner conductor 25c, than in the lower section of the sensor head, below the inner conductor 25c. These magnets which may be composed of (but not limited to) rare earth neubidium type magnetic material, may be attached to the outer conductors 25a, 25b with the ability to slide along them in the Y-direction within chambers 33, 34.

The position of magnets 31, 32 can be controlled by air pressure inside the chambers 33, 34 by an external air pump connected thereto via pipes 35, 36. The movement of magnets 31, 32 provides a means for modifying the strength/amplitude of magnetic field Bp in the region 30, while not changing its direction significantly. The magnets' poles (N-S) direction is perpendicular to the probe's main axis (the Y axis). That is, the poles are aligned with the Z-axis.

The transmission line section of the sensing head 20 may be of different types, dimensions, impedances, materials, etc., as long as it kept magnetically transparent in the region where field Bp is generated by the magnets. The ending of the transmission line section can be of various shapes and types depending on how deep the RF radiation is to penetrate into the examined tissue ET. For example, the sensing head can be ended as a wide band antenna, which could be of the type, for example, of a conical antenna in the case of a coax line, or a dipole antenna, or a V-shaped antenna, or a strip line antenna (the two ground strips being opened gradually to the sides) in the case the line is flat. The transmission line can be also left open-ended, or can be ended by a surface coil or by a side emitting leaky end. The preferred way is to form an open cavity at the end of the transmission line and let a small part of the tissue penetrate into the open cavity of the TL. In this way, the RF fields can be considered as with known geometrical configuration (the TL modes) inside the sensing head and near its end, and the RF fields will be transmitted only into a small proximal volume of the tissue, with little radiation transmitted into the remainder of the body.

The additional receiving coils 27, 28 are positioned so that they will detect magnetic fields in a direction perpendicularly to both the Bp and the B-RF magnetic fields. Thus, they will be able to detect the NMR signal in the XZ plane, a direction in which the transmission line TL defined by the conductive strips 25a–25c cannot detect the NMR signals. Their design could be of the types known in the literature, such as: surface coils, single coils, multi-turn coils, saddle coils, etc.

FIG. 4 schematically illustrates the various fields present in the region 30 at the distal end of the transmission line defined by conductive strips 25a–25c. Thus, the substantially homogenous polarizing magnetic field generated by the permanent magnets 31, 32, is shown as magnetic field Bp; the magnetic field generated by the transmission of the RF pulses from the distal end of the transmission line is indicated by magnetic field B-RF which, as indicated earlier, extends in one direction between conductive strips 25c and 25a, and in the opposite direction between conductive strips 25c and 25b; and the electric field generated by the transmission of the RF pulses from the distal end of the transmission line is indicated E-RF. As indicated above, the additional receiving coils 27, 28, when included, serve as additional receivers for detecting the NMR signal components along an axis orthogonal both to Bp (the polarizing magnetic field by the permanent magnets 31, 32), and B-RF (the magnetic field generated by the transmission of the RF pulses from the distal end of the transmission line). Coils 27, 28 are orthogonal to the transmission line main axis (the Y-axis), so that the RF coils 27, 28 detect NMR signals in the Y-direction.

The signal fed into the probe sensing head 20 through the transmission line defined by conductive strips 25a–25c, is of the form of a train of repetitive pulses. The repetitive pulse train, called the RF sequence, consists of combinations of repetitive pulses in which some are optimized for EI measurement, and some are optimized for NMR measurement. The NMR pulses can be, for example, from one of the known (in the literature) NMR sequences. For example, a combined sequence schematically may be as follows: First, an EI optimized set of pulses, e.g., a short nano-second pulse train followed by a time break, in which the reflection is collected with a very high sampling rate. This is followed by an NMR optimized set of pulses; for example, the NMR pulses can be the known inversion recovery, simple spin echo, Carr-Purcell-Meiboom-Gill echo train, stimulated echo, etc.

Figure 5:
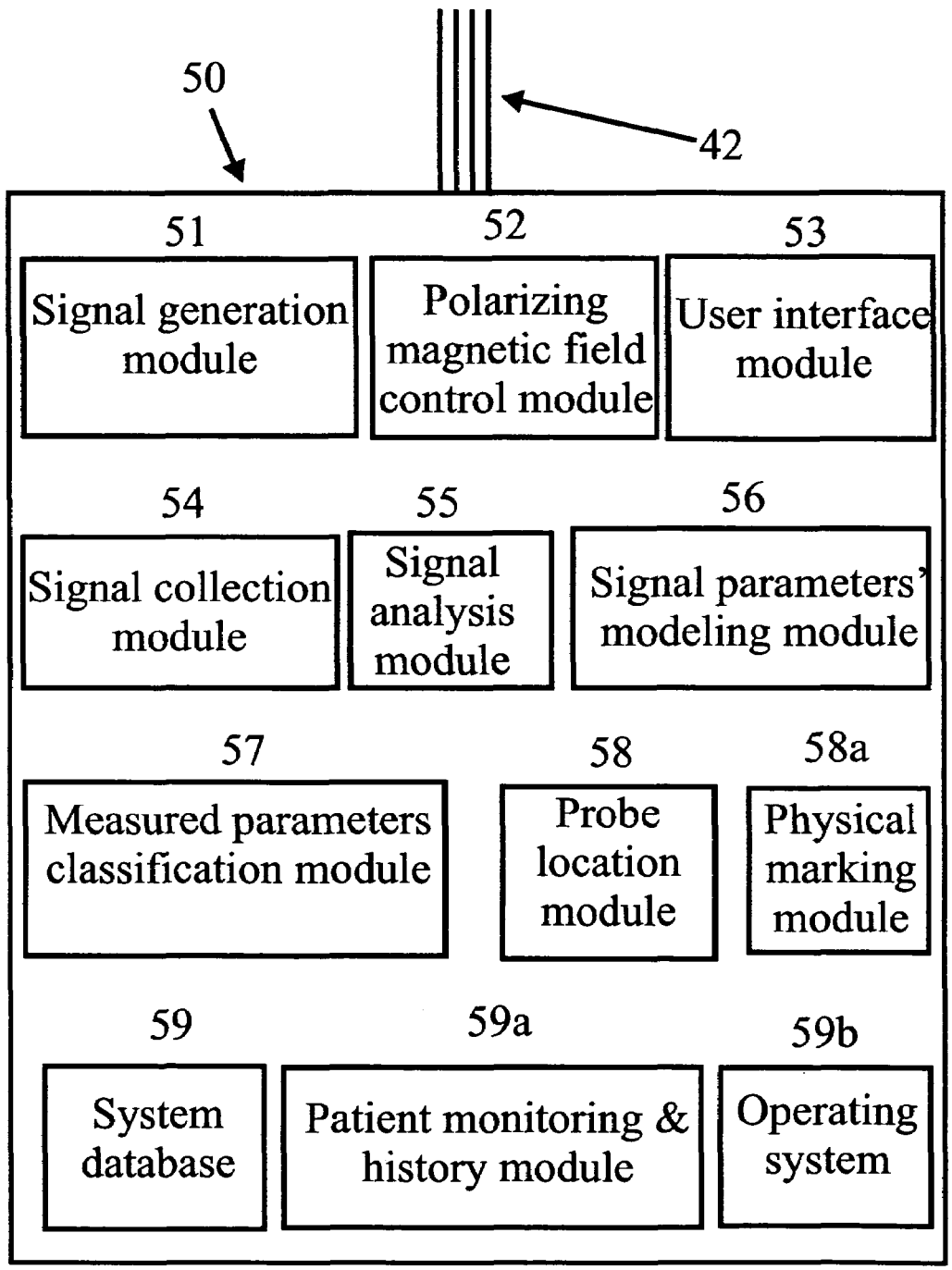
FIG. 5 is a block diagram illustrating the major components or modules in the apparatus of FIGS. 2–4.
Figure 6:
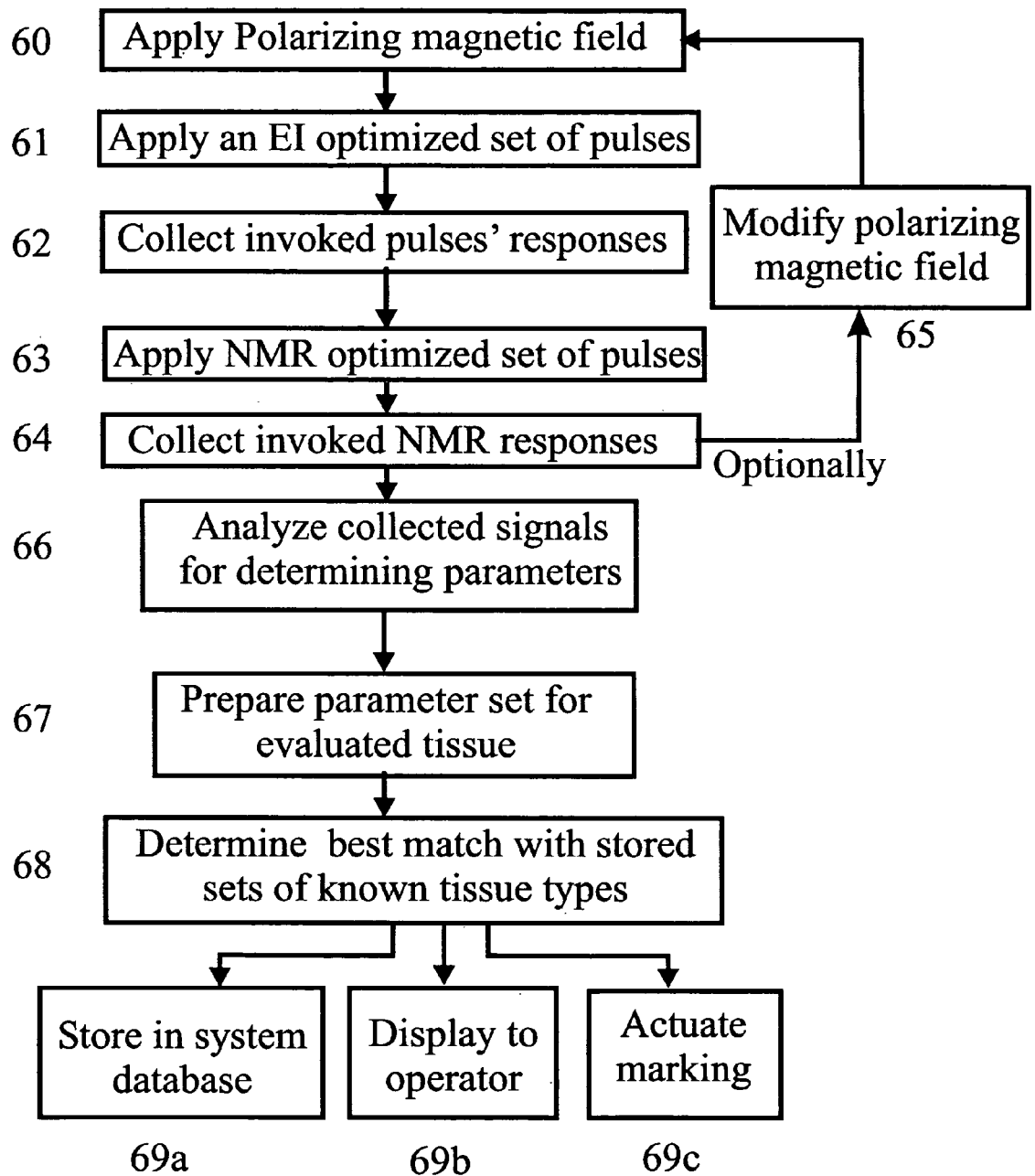
FIG. 6 is a flow chart illustrating a preferred mode of operation of the apparatus of FIGS. 2–5.

FIG. 5 is a block diagram illustrating one form of apparatus constructed and operating in accordance with the present invention as describes above; and FIG. 6 is a flow chart illustrating the operation of such an apparatus when used to examine tissue for distinguishing cancerous tissue from non-cancerous tissue. To facilitate understanding, the block diagram illustrated in FIG. 5 identifies the main components of the apparatus illustrated in FIG. 2 with corresponding reference numerals.

Thus, FIG. 5 illustrates the flexible cable set 42 (which contains the transmission line TL carried by probe 10 and having a distal end occupied by the sensor head 20 adapted to be brought into contact with the tissue to be examined) that connects the probe 10 to the processing unit 50 (FIG. 2). FIG. 5 also illustrates the controls, located within the processing unit 50, for applying and receiving RF pulses via the transmission line TL and sensor head 20 to the examined tissue ET, which pulses are capable of invoking electrical impedance (EI) response signals corresponding to the electrical impedance of the examined tissue, and nuclei magnetic resonance (NMR) response signals corresponding to the NMR properties of the examined tissue. As described above, control circuitry within processing unit 50 also controls the sensor head 20 to detect the EI and NMR response signals, and to feed them via transmission line in flexible cable set 42 to the processing unit 50 for analyzing the detected response signals and for determining therefrom the type of tissue examined, e.g., cancerous or non-cancerous tissue. This determination is indicated to the user by an indicator in probe 10. The determination may also be used to actuate a marker for marking the tissue according to the tissue-type determination.

Thus, as shown in FIG. 5, the controls within the processing unit 50 include a signal generation module 51 capable of generating programmable electric pulses up to 5 GHz; a polarizing magnetic field control module 52 for controlling the polarizing magnetic field (Bp) within region 30 occupied by the examined tissue; and a user interface 53.

The user interface 53 module controls the display unit, an audio unit, optionally a marking unit control, and a control panel. Some of the operation controls and indicators can be mounted on the probe handgrip unit. The main functions of the user interface are to control the operation of the system and to display (in visual and/or audio form) the outputs of the processing unit 50 in a way that will be informative to the user.

The control of the polarizing magnetic field may be effected by changing the position of the permanent magnets 31, 32 (FIG. 3*a*) of the sensor head 20. One way to perform this is by a mechanical push/pull shaft mechanically connected to the magnets and mechanically controlled by control module 52. Another way of moving the magnets is by the use of a vacuum assisted shaft. The magnets are mechanically connected to a short shaft at their remote (relative to the distal end of the probe head) end. The short shaft is connected at its opposite side to an air piston. The air piston is inserted into an air tube that is connected to a pulsed vacuum pump at the external unit side. Each time the air pressure is reduced in the tube, the magnets are pulled back and vice versa.

According to another embodiment of the invention, the polarizing magnetic field would be produced and controlled by electromagnets, in which case the change in the polarizing magnetic field would be effected by a change in the location of, or the current through the coils generating this polarizing field. Another alternative would have the coils surrounding a paramagnetic core, in which case the change in the polarizing magnetic field would be effected by a change in the induced magnetic field in the core due to a change of current in the surrounding coils.

The control and indicator circuitry within the processing unit 50 would further include a signal collection and digitizing module 54 for detecting the excitation RF pulses the reflected RF pulses and the NMR pulses. A preferred way of detection is by digitizing voltages along the transmission lines using an analog to digital converter module. Preferably the digitizer sampling rate is controlled so as to be able to reach up to twice the signal generator maximal frequency.

The signal collection and digitizing module 54 communicates with a signal analysis module 55. The signal analysis module is a computer program made up of a set of software routines. It receives as an input the measured signals in the form of a set of vectors, and removes noises and artificial effects from the signals. Its output is the set of "clean" processed signals.

As further shown in FIG. 5, the processing unit further includes a signal modeling module 56, a classification module 57, and a data-base module 59.

The signal-modeling module 56 is a computer program, made up of a set of software routines, which calculates a set of parameters that characterize the measured tissue. The data-base module 59 stores a database of various types of tissues and their characterizing set of parameters, including their statistical dispersion properties.

The classification module 57 is a computer program, made up of a set of software routines, which looks for similarities between the measured set of parameters outputted from the modeling module 56, and the pre-recorded set found in the data-base module 59. One simple similarity estimator is the distance of the measured points, in the multi-dimensional parameter data-space, from the location of each one of the prerecorded groups, defining specific tissue types. The most similar group (best-match) defines the type of the examined tissue ET.

The determination of the classification module 57 is outputted via flexible cable set 42 to a tissue characterization indicator 40 within the hand-held probe 10, which displays to the user the determined tissue type.

The processing unit 50 may also include a probe location module 58, and a physical marking module 58*a* controlled by the classification module 57 in the processing unit 50.

Marking module 58*a* controls the operation of marking a measured spot on the tissue by an appropriate physical mark when instructed by the processing unit 50. It uses a detectable material to physically mark the location of measurement. The detection of the marking can be immediate or delayed by the user. The simplest way to perform the marking is by the use of visually detectable substance, e.g., a three color biological marking ink, emitted from a jet nozzle mounted at the tip of the probe. After tissue recognition has been performed, a printing order is sent to the jet nozzle and the appropriate color dot is printed.

Other forms of detectable marking material can be, for example, a physical marker conjugated to antibodies, metal balls, IR paint, etc. The marker can also be a solid marker like a small metal pin, or a combination of solid balls painted with a distinguishing color. The solid balls are palpable and the color is visible. The marker can also be detectable by other known modalities, like X-ray or ultrasound.

As further shown in FIG. 5, processing unit 50 further includes a patient monitoring and history module 59*a*, and an operating system, generally designated 59*b*, namely the computer software that controls and coordinates all the operations of the hardware and software components of the apparatus.

Reference is now made to the flow chart illustrated in FIG. 6 describing the overall operation of the apparatus.

Thus, the user grips probe 10 and brings the sensing head 20 at the distal end of the transmission line TL into contact with tissue ET to be examined. When this contact is established, probe 10 applies a repetitive train of RF pulses, called an RF sequence, through the transmission line, defined by the conductive strips 25*a*–25*c*, which pulses invoke electrical impedance (EI) response signals corresponding to the electrical impedance properties of the examined tissue, and nuclear magnetic resonance (NMR) response signals corresponding to the NMR properties of the examined tissue. As indicated above, the RF sequence of pulses consists of some pulses optimized for EI measurement and other pulses optimized for NMR measurement. The response signals evoked by the applied sequence of RF pulses are detected by the sensor head 20 and processed by the processing unit 50 to determine the type of tissue examined.

The foregoing operations are briefly illustrated in the flow chart of FIG. 6. Thus, as shown in FIG. 6, the system first sets a polarizing magnetic field (block 60). The system then applies an EI optimized set of pulses to the examined tissue (block 61) and collects the invoked pulse responses (block 62), which in this case would be reflected pulses reflected from the open end of the transmission line TL. The system also applies an NMR optimized set of pulses (block 63) to the tissue, and collects therefrom the NMR responses (block 64). The detected response signals would thus provide information as to two modalities of the examined tissue, namely its EI properties and its NMR properties.

Optionally, to provide better information concerning a third modality of the examined tissue, the polarizing magnetic field (Bp), produced by the permanent magnets 31, 32 is modified as described above (block 65), and the operations of blocks 60–64 are repeated to obtain the corresponding information when the examined tissue is subjected to the modified polarizing magnetic field.

The signals collected in the above-described operations are analyzed for predetermined parameters (block 66), and a parameter set is prepared for the examined tissue (block 67). The parameter set prepared for the respective examined tissue is then compared with stored parameter sets of known tissue types as described above, and a best-match determination is made to identify the type of the examined tissue (block 68).

It will thus be seen that the detection process is comprised of the following four operations: (1) signal collection/acquisition; (2) signal analysis; (3) signal parameters' modeling; and (4) classification of measured parameter set to known tissue type parameter set, prerecorded and saved in the memory bank of the system.

The collection of the signals is made by fast digitizing, using multiple acquisition channels. The analysis is made by the application of signal processing routines that clean the signals from noise and artificial affects.

The modeling is made by a compression process that characterizes a signal by a relatively short array of parameters, and mathematically transforms the parameters to an orthogonal set of parameters. For example, a 10000 point acquired signal can be characterizes by an array 10 of parameters. The modeling is done both in the frequency domain and in the time domain.

The classification is performed by a best-match comparison of the measured parameters to known tissue parameters stored in the memory together with their statistical dispersion parameters, and by identification of similarities between the just measured parameter set and a specific tissue type group of parameters.

Following this comparison, the just examined tissue type is characterized, and that information is, for example, stored in the system data-base (block 69a), displayed to the operator (block 69b), used to actuate a marker to mark the tissue (block 69c), or used in any other way needed, according to the specific procedure performed.

FIGS. 7a–7d provide schematic illustrations of the synergistic EI response and NMR response of the examined tissue following the irradiation by a single pulse generated by the main unit's signal generator.

FIG. 7a shows the form of the excitation pulse generated. In this example it is a pulse of the length of a few tens of microseconds, which will invoke both an EI response and an NMR response. It is a pulse of the so-called 90 degree pulse type, know in the NMR literature.

FIG. 7b shows the response of the tissue to the excitation pulse shown in FIG. 7a detected by sensor head 20 in the TL. The response is delayed by a time interval $t_1$ due to the length of the TL, and is composed of two types of signals.

The first (temporal) part, in time interval $t_2$, is the EI response of the tissue, which "follows" the form of the excitation pulse in FIG. 7a, but distorts it because of the frequency-dependent dielectric properties of the tissue and the absorption by the nuclear magnetization vector. The second part in time interval $t_3$ is the free induction decay (FID) of the NMR signal generated by the relaxation of the nuclear spin magnetization vector in the examined tissue (region 30, FIG. 3a) back to the direction of the Bp field (see FIG. 4), following the "excitation" by the "90 degree" pulse in FIG. 7a. FIG. 7c shows a close up view of the signal in time interval $t_1$ and $t_2$. In this time segment, the reflected EI pulse is similar to the incident pulse, but is distorted because of the tissue impedance and NMR absorption.

In FIG. 7d is shown the response of the tissue to the excitation pulse shown in FIG. 7a, detected by the RF coils 27, 28. In this channel, the response is composed only of the FID of the NMR signal generated due to the relaxation of the nuclear spin magnetization vector in the examined tissue in region 30 back to the direction of the Bp field (see FIG. 4) following the excitation by the excitation pulse in FIG. 7a. It is to be noted that, since the directions of detection (with regards to the NMR signal) of the coils is orthogonal to that of the transmission line TL, the FID response is phase-shifted by 90 degrees relative to the FID signal detected by the transmission line TL (see FIG. 7b).

The transmitted radiation's spectrum is determined by the form of the pulse, and by the design of the sensor. The spatial form of the radiation (lobe structure, etc.) is determined by the geometry of the sensor head 20 at the distal end of the transmission line TL. Since the examined tissue is in close proximity to the distal end of the transmission line, pulses reflected back into the transmission line because of the impedance differences between the tissue and distal end of the transmission line, provide direct information regarding the dielectric properties/response of the tissue. These are the signals in time interval $t_2$ in FIGS. 7b–7d. The pulse form, duration, repetition, and sequence structure, are designed, and are also controlled in real time, so that they will provide the maximal (S/N) resolution for differentiating between different types of tissue.

As indicated earlier, the tissue measurement is based on a comparison of the incident pulse to the reflected pulse, and on the analysis of the FID, and results in a series of parameters characterizing the tissue; whereas the detection of cancerous tissue sections is based on the comparison of the, just measured, tissue parameters with the parameters defining various tissue types stored in the memory bank.

The external polarizing magnetic field (Bp) generated by the magnets 31, 32, aligns the spins, and particularly nuclear spins of the nuclei (preferably proton/hydrogen) parallel to the aligning magnetic field lines. This generates a "nuclear magnetization vector" in the tissue volume 30. The geometric orientation of the transmission-line transmitted RF pulses is such (see also FIG. 4) that these RF pulses serve as an RF "deflecting" magnetic field for the "nuclear magnetization vector", as is performed in numerous NMR procedures and set-ups.

The NMR FID following the relaxation of the magnetization vector, which follows after the RF pulse has been transmitted, is detected by the sensor head 20, providing detection of the NMR response of the tissue. The RF energy absorbed by the magnetization vector, as it is rotated during the RF pulse duration, is also detected, as a change in the spectrum of the dielectric response of the tissue examined.

Additionally, but not necessarily, the RF receiving coils 27, 28 (FIG. 3a) detect the NMR FID signal components in the direction perpendicular to the transmission line TL receiving direction. This measurement provides additional information and a better signal-to-noise ratio, and is correlated with the NMR signals detected by the transmission line. This will improve the NMR signal detection abilities and sensitivity of the probe.

The NMR response of the tissue is detected in three different ways by the system: 1) as an absorbance in the reflected RF pulse contributing to the effective calculated impedance; 2) as an FID following the RF reflected pulse; and 3) as an FID detected by the RF coils 27, 28. The significant NMR measured tissue parameters are, but not limited to proton density (PD), longitudinal relaxation time (T1) and/or transverse relaxation time (T2).

The magnetic fields generated by the magnets 31, 32 may have a gradient in the Y direction (the direction along the probe axis). This will shorten the duration of the NMR response and weaken the signal due to NMR line broadening. The pulse sequence is designed to take these issues into account. Alternatively (not shown), the magnets could be arranged in a form that will minimize the gradient in the Y-direction (the direction along the probe axis) of the field generated by the magnets. The pulse sequence would then be designed differently from the case when there is a significant gradient in the field, in order to obtain the best SNR for the NMR signal.

As described above, the magnets 31, 32 generating the Bp may also be moved during the measurement process. The movement is in the Y direction (the direction parallel to the probe axis). This movement will generate changes in the amplitude, and may also generate slight changes in the direction/orientation of Bp. Alternatively, as indicated earlier and as described below, the amplitude of Bp can be controlled by using coils and/or paramagnetic cores driven by coils. The effects would be the same as when physically moving permanent magnets.

This movement will serve a number of purposes: First, it will enhance detection sensitivity by the use of lock-in techniques. Secondly, since the external magnetic field is non-homogeneous, movement of the magnets translates to a change in the NMR resonance frequency (for a given spin) at a given distance from the probe tip. By controlling the resonance frequency and, separately, the form, duration, and rate of repetition of the RF pulses, additional information is obtainable regarding the NMR response of the tissue at a given distance from the probe tip. This will provide better characterization of the tissue's NMR response.

The movement of the magnets can also be used to provide information regarding the depth at which a change in the type of tissue occurs. The magnets are moved so that the field Bp strength at a given distance from the probe tip will be set to a chosen value. The RF pulses will be generated so as to enhance the NMR response from distances greater than the chosen distance from the probe tip. The differences in response of different types of tissue, at that chosen distance from the probe tip, can thus be used to locate the change in the type of tissue.

A Number of Possible Variations

FIGS. 8–14 illustrate a number of possible variations that may be made in the above-described apparatus.

Figure 8A:
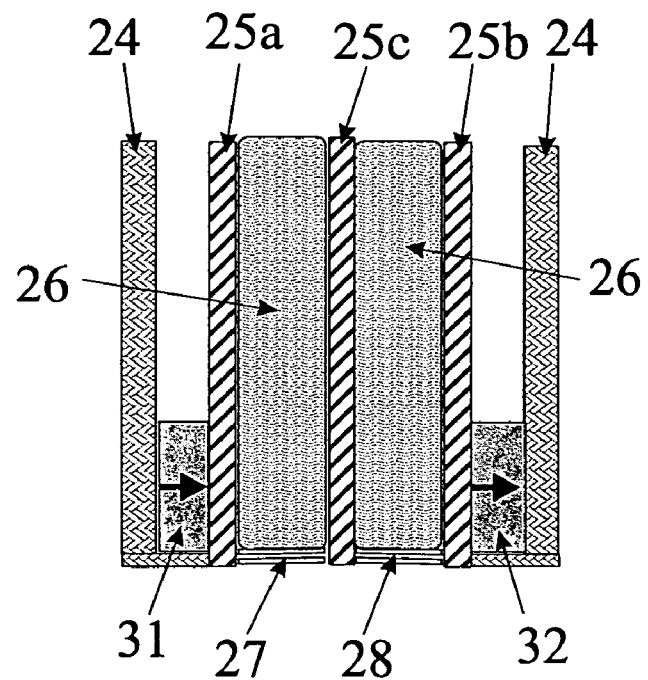
FIGS. 8a–8m illustrate a number of possible variations in the polarizing magnetic field and the transmission line ending in the apparatus of FIGS. 2–6.

FIG. 8*a* illustrates a variation wherein the inner conductive strip 25*c*, defining the inner conducting trace of the probe head, making it flush with the outer conductive strips 25*a*, 25*b* defining the ground plates. The ends of the magnets 31, 32 could be flush with, or protruding, relative to the inner conducting trace 25*c* and ground plates 25*a*, 25*b*. The RF coils 27, 28 are then also moved to the probe distal end. The substance volume sampled is situated directly in contact with the probe end.

Figure 8B:
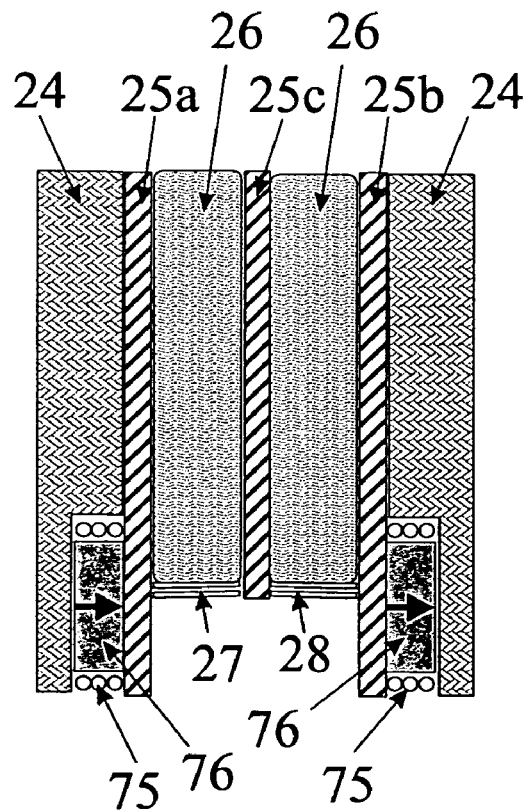

FIG. 8*b* illustrates a variation wherein the magnets are replaced by coils 75 surrounding paramagnetic cores 76, generating the polarizing field when current is driven through the coils. In this variation, the change in the amplitude of the polarizing field is performed by changing the intensity of the current through the coils. This current change induces a change in the magnetic field of the paramagnetic cores.

In another variation (not illustrated), the magnets could be replaced by coils, which will generate the polarizing field when current is driven through them. In this variation, the change in the amplitude of the polarizing field is performed by changing the intensity of the current transferred through the coils.

Figure 8C:
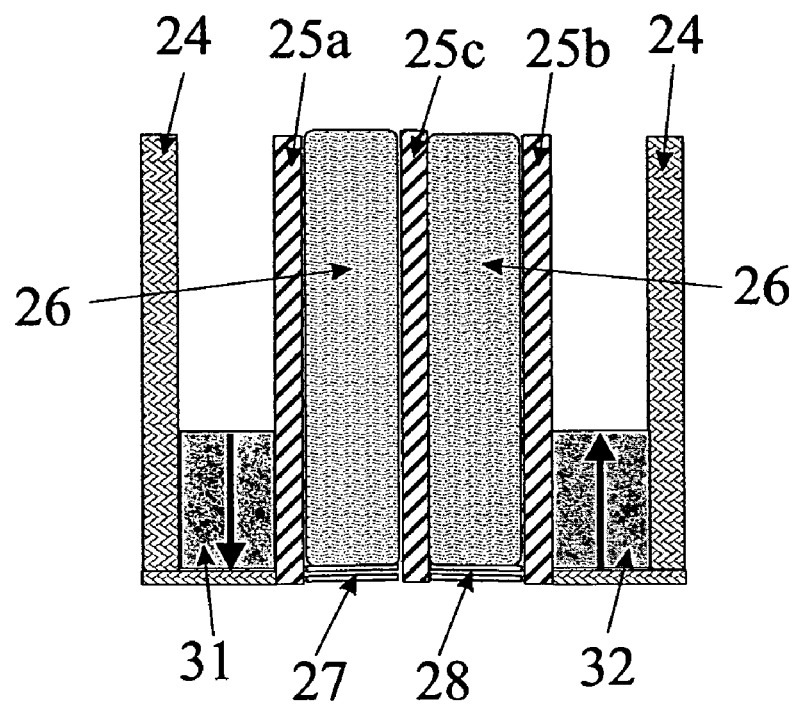

FIG. 8*c* illustrates a variation wherein the poles of the magnets 31, 32 are oriented in a direction parallel to the main axis of the probe head (the Y-direction, as defined for the preferred embodiment).

Figure 8D:
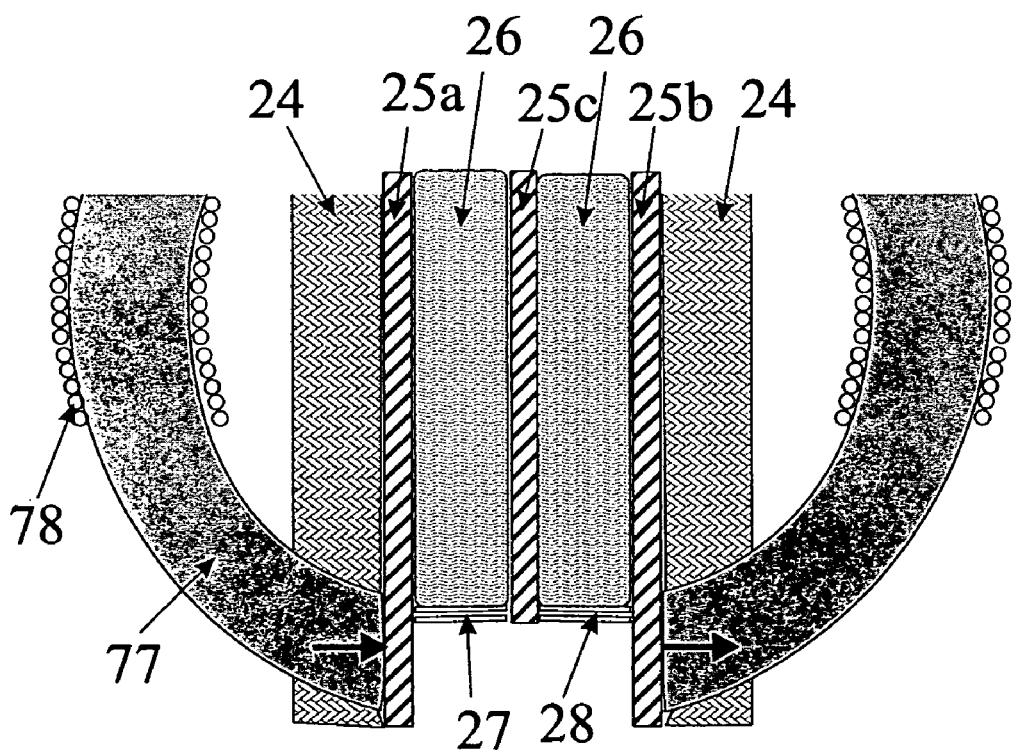

FIG. 8*d* illustrates a variation wherein the polarizing magnetic field is generated by a "horse-shoe" shaped paramagnetic core 77, driven by a surrounding coil 78.

Figure 8E:
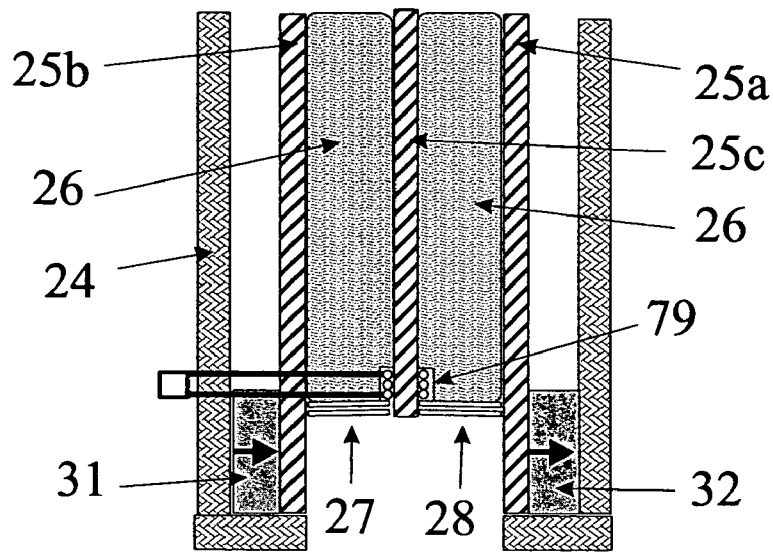

FIG. 8*e* illustrates a further variation wherein a current sensor, in the form, for example, of a pick-up coil 79, is placed near the distal end of the probe head to measure the current that passes through the examined substance. With this configuration a direct measurement of impedance can be made.

Figure 8F:
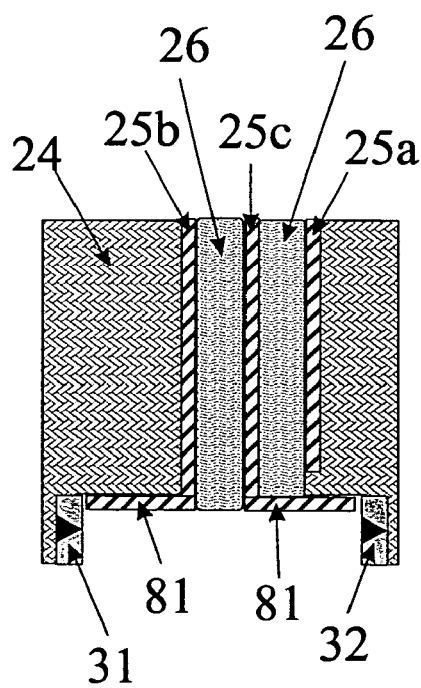
Figure 8G:
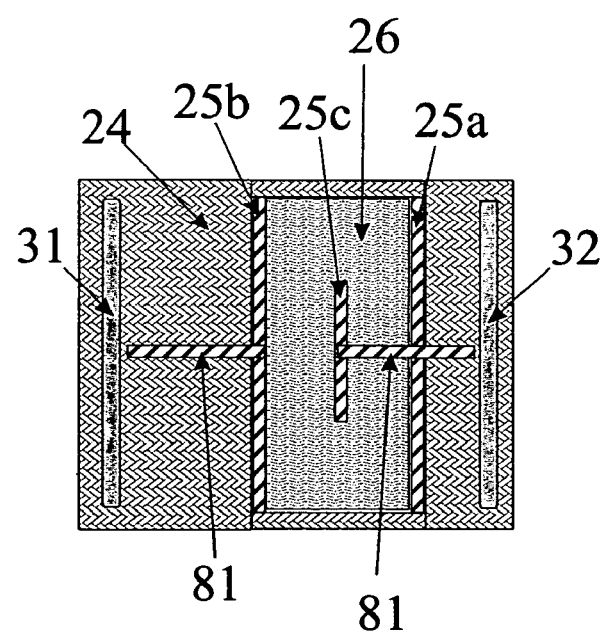
Figure 8H:
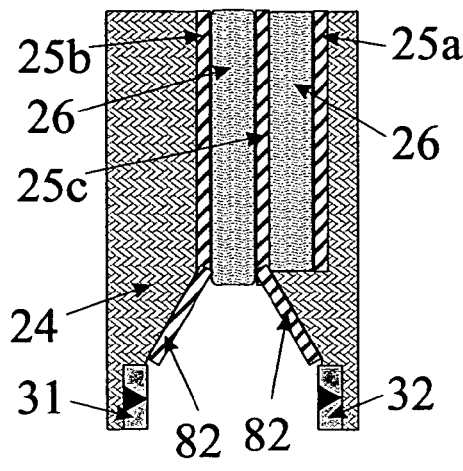
Figure 8I:
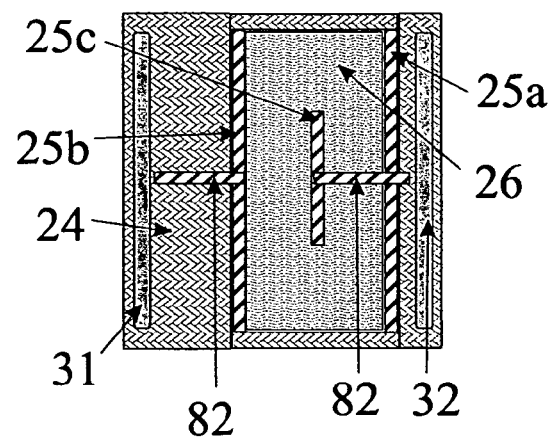
Figure 8J:
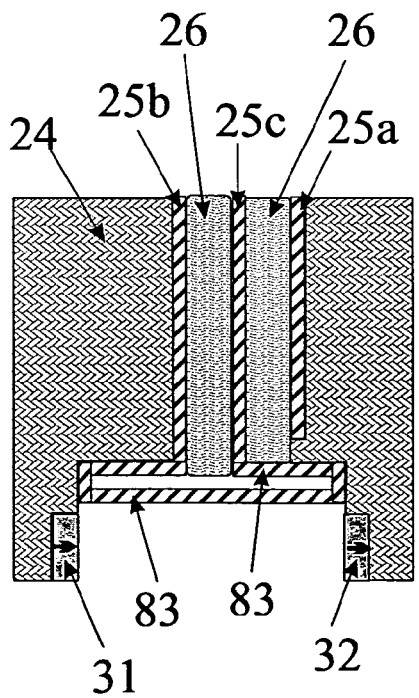
Figure 8K:
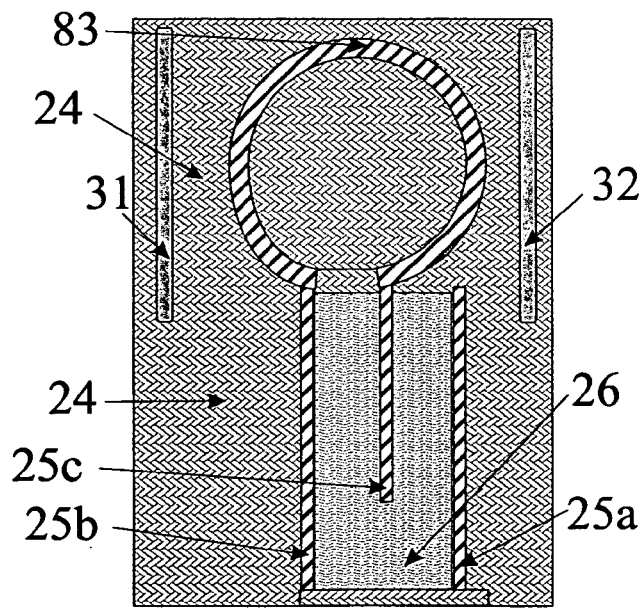

FIGS. 8*f*–8*k* are side and plan views illustrating further variations in the transmission line end structure: FIGS. 8*f*, 8*g* illustrate one ended by a dipole antenna 81. FIGS. 8*h*, 8*i* illustrate one ended by a V-shaped antenna 82; and FIGS. 8*j*, 8*k* illustrate one ended by a surface coil 83.

Figure 8L:
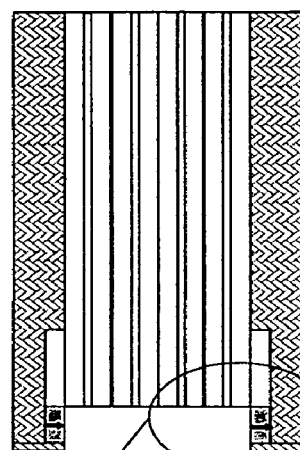
Figure 8M:
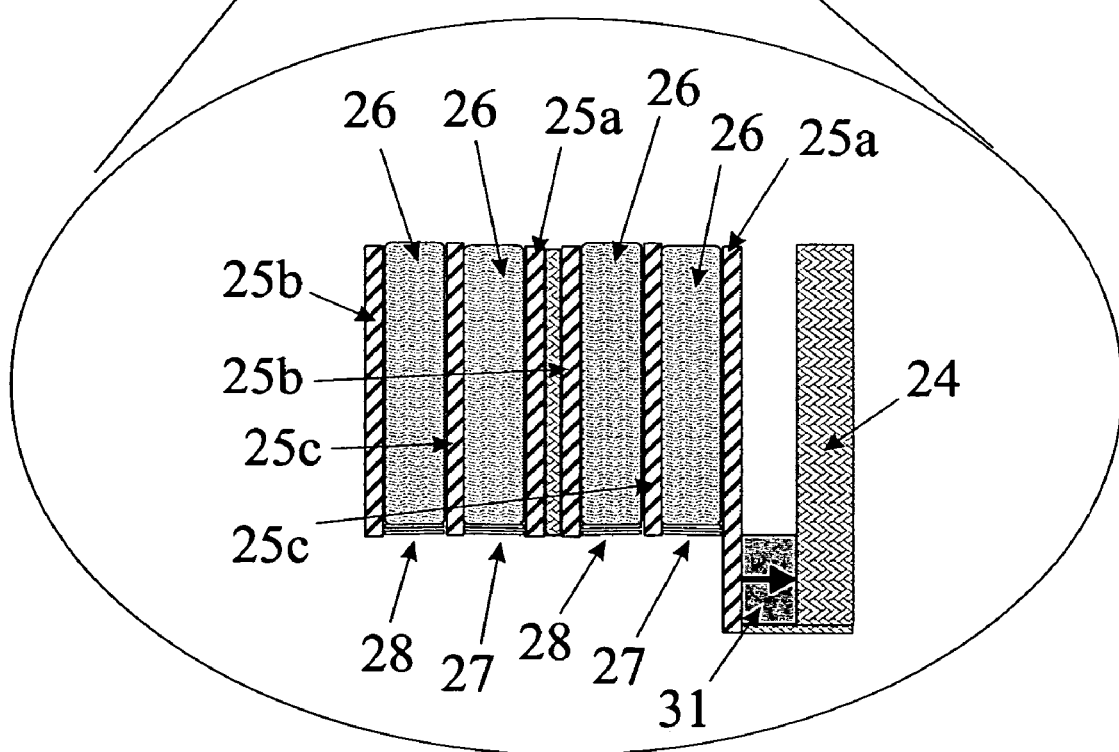

FIGS. 8*l*, 8*m* are side and enlarged views, respectively, illustrating yet another embodiment including an array of miniature sensors all sharing the same source of polarizing magnetic field 31, but each using different sources of RF radiation.

Figure 9A:
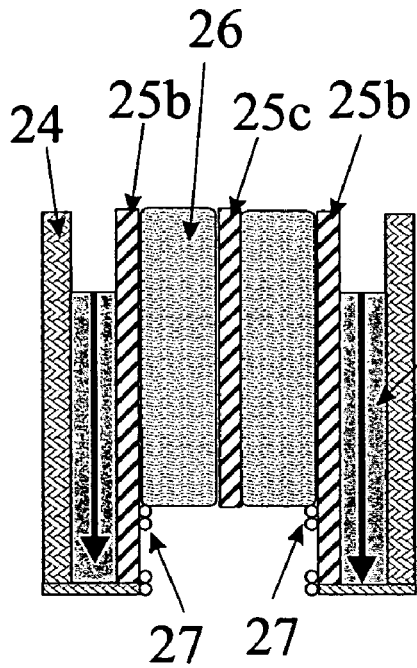
FIGS. 9a–9f illustrate further possible variations in the configurations of the polarizing magnetic field and transmission line.
Figure 9B:
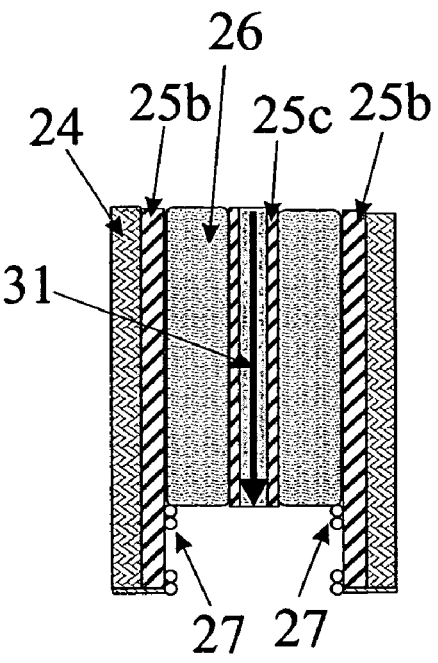
Figure 9C:
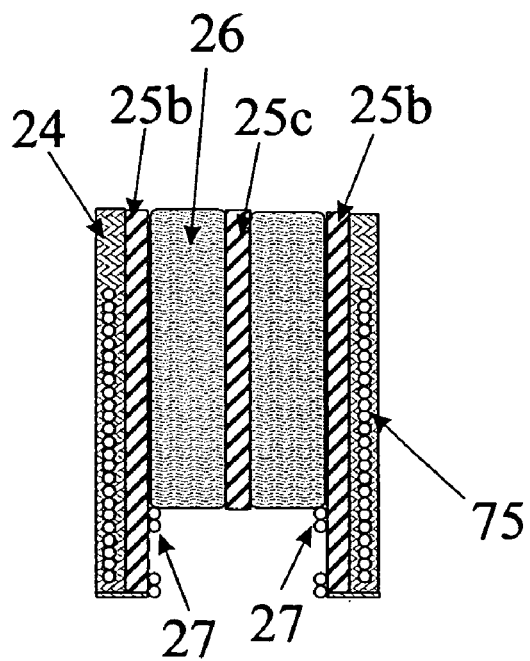
Figure 9D:
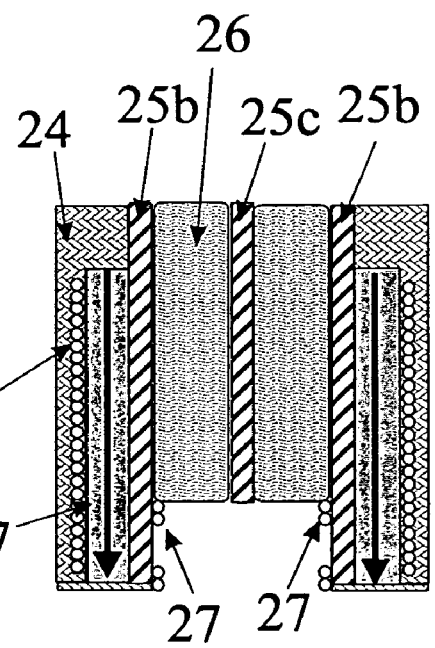

FIGS. 9*a*–9*d* illustrate further embodiments of the invention wherein the transmission line TL is of the cylindrical co-axial line type, having an inner conducting core 25*c*, surrounded by an insulator 26, which in turn is surrounded by a conductive cladding 25*b*. The polarizing magnetic field is generated by a movable concentric magnet 31, either surrounding the transmission line TL (FIG. 9*a*), or surrounded by the transmission line TL (FIG. 9*b*). In another variation, the magnet is replaced by coils 75 (FIG. 9*c*), or by coils 78 surrounding a paramagnetic core 77 (FIG. 9*d*). In the co-axial geometry, there is only one additional RF receiving coil needed. This coil is indicated in FIGS. 9*a*–9*d* by 27.

Figure 9E:
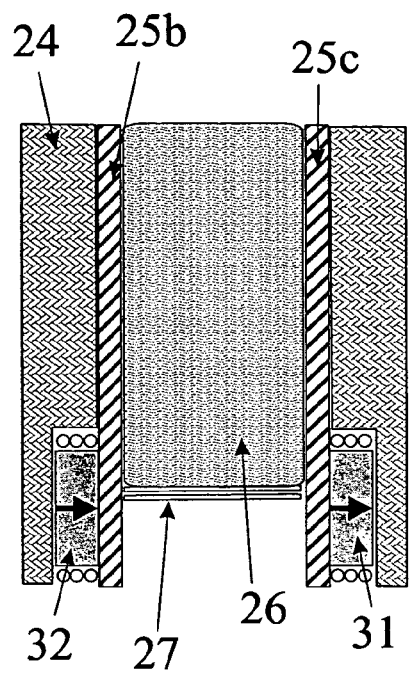
Figure 9F:
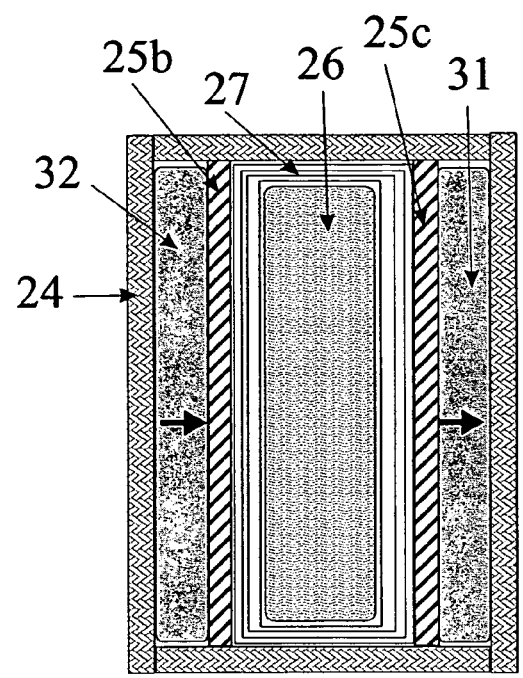

FIG. 9*e* (end view) and FIG. 9*f* (plan view) illustrate a further variation wherein the transmission line section is made of two conducting strips only, without an inner trace. One strip 25*b* serves as the ground plane, and the other strip 25*c* serves as the signal plane. With this configuration, only one RF coil 27 is needed in order to additionally collect NMR signals from the tissue.

Figure 10:
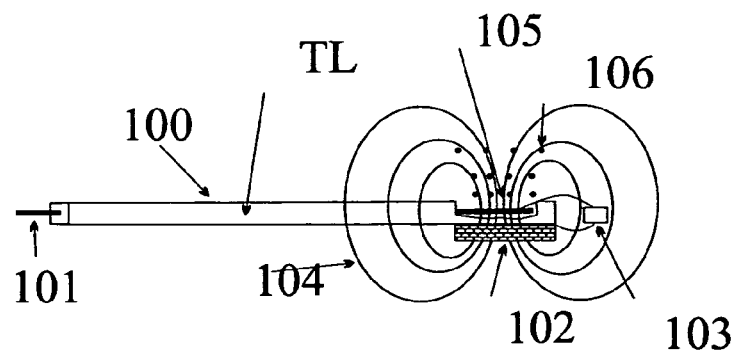
FIG. 10 diagrammatically illustrates a leaky transmission line configuration of sensor head in accordance with the present invention.

FIG. 10 illustrates another embodiment wherein the transmission line TL is open-sided and leaky. Thus, a section of the outer conductor 100 of the transmission line TL is cut off and forms a window 105. The inner conductor 101 continues up to the end of the transmission line TL. The inner conductor is electrically connected to an impedance tuning circuit 103. A permanent magnet 102 is placed below the transmission line. In this configuration, the polarizing field lines 104 of the permanent magnet have a component in the window zone perpendicular to the B-RF field 106 which in FIG. 10 extends outwardly from the page plane. The measurement is performed by advancing the probe so that the sampled tissue is positioned in the window 105.

Figure 11:
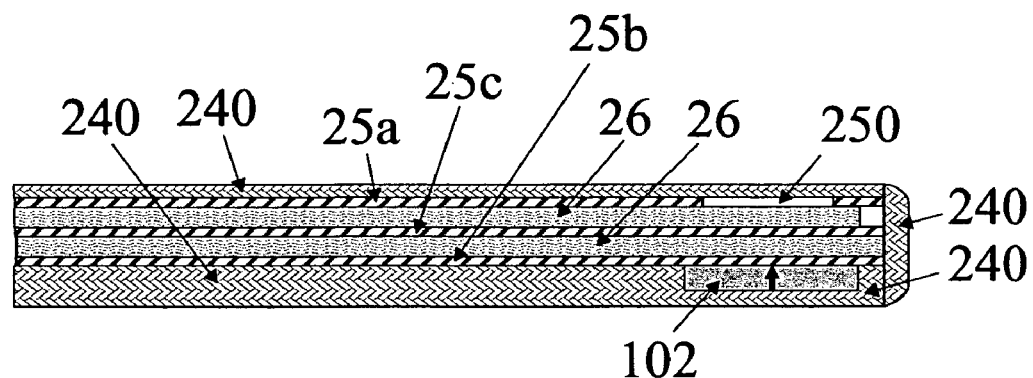
FIG. 11 illustrates the invention embodied in a catheter for insertion into the lumen of the patient's body.

FIG. 11 illustrates yet another embodiment wherein the sensor head of the probe is placed on the distal end of a catheter and inserted into a lumen of the body for inspection of the lumen walls. As also in the case of FIG. 10, the cut-off section of the outer conductor 250 allows for analysis of tissue near the region 250. The probe is covered by the catheter cladding 240.

Figure 12:
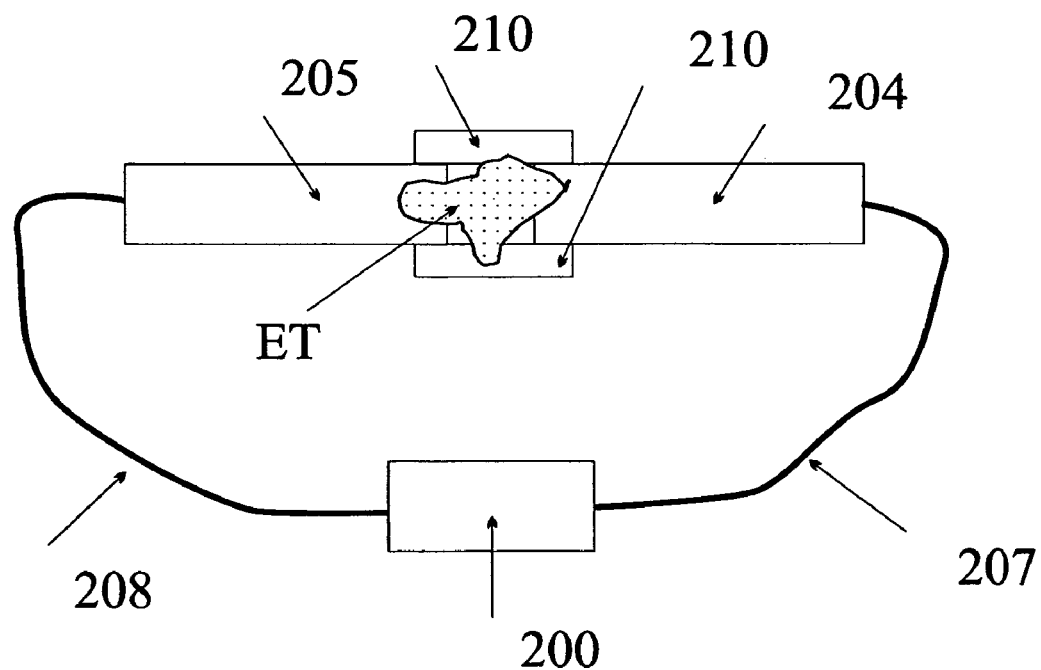
FIG. 12 illustrates apparatus constructed in accordance with the present invention including two sensor heads to be applied to opposite sides of the tissue being examined.

FIG. 12 illustrates another embodiment wherein two probes are used in a transmitter/receiver configuration. In this configuration, one probe 204 acts in its turn as the transmitter, transmitting signals through the examined tissue ET, and the other probe 205 receives those signals and then in its turn act as a transmitter, while the first one acts as a receiver. In this mode of operation, both the reflected and transmitted signals are detected. The transmitted signals are fed through one transmission line 207, and the detected signals are transferred through another transmission line 208. Both transmission lines connect to the main unit 200. Magnets 210 are positioned so that they will generate the necessary polarizing field.

Figure 13:
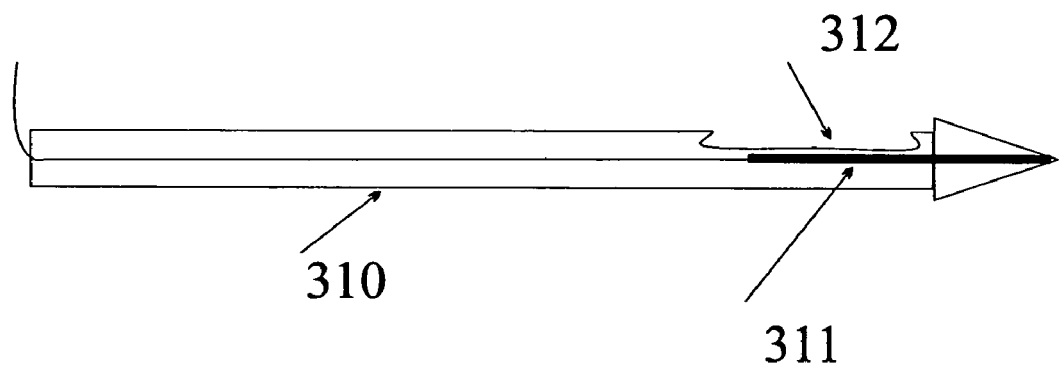
FIG. 13 diagrammatically illustrates a sensor head in accordance with the present invention incorporated in a biopsy needle.

FIG. 13 illustrates another embodiment wherein the sensor head of the probe 311 is placed inside a biopsy core needle 310. The probe continuously inspects the tissue type at the tip of the needle, as the needle is passing, from the outer skin surface to the biopsy site. Suspected tissue will be excised, for example, using a tissue-collecting cavity 312.

Figure 14:
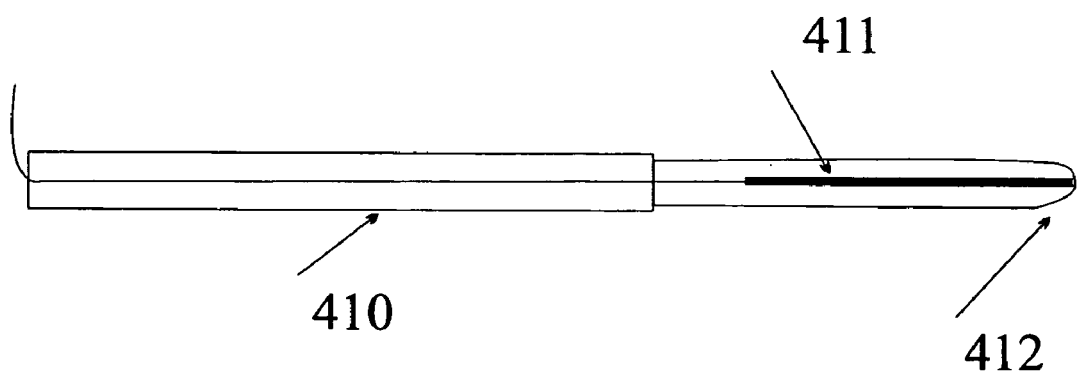
FIG. 14 illustrates a sensor head constructed in accordance with the present invention incorporated in a cutting tool so as to enable obtaining an indication of the tissue type in real time during a surgical operation.

FIGS. 14 illustrates yet another embodiment wherein the sensor head of the probe 411 is conjugated to a cutting tool, comprised of a handle 410 and a cutting head 412, so that tissue recognition may be made prior to each excision cut.

In the above described embodiments, contrasting agents (for example: gadodiamide or mangafodipir) for the enhancement of the NMR signal for the characterization of various tissue parameters may also be applied to the examined tissue, either locally, or intravenously.

The RF sequence fed into the sensor through the transmission line may consist of combinations of repetitive pulses, some optimized for the EI measurement and some optimized for EPR (electron paramagnetic resonance) measurements. The polarizing magnetic field may also be optimized for the detection of EPR signals. Contrasting agents (for example: activated charcoal, or cabamoyl-proxyl, or trityl-methyl based OX 031, OX036) to the enhance the EPR signal for better characterization of various tissue parameters, may also be applied to the examined tissue, either locally or intravenously.

The RF sequence fed into the sensor through the transmission line may also consist of combinations of repetitive pulses in which some are optimized for the EI measurement, and some are optimized for Proton Electron Double Resonance (PEDR), also known as Overhauser MR, measurements. The polarizing magnetic field is also optimized for the detection of PEDR signals. Contrasting agents to enhance the Overhauser signal for the better characterization of various tissue parameters, may also be applied to the examined tissue, either locally, or intravenously.

It will also be appreciated that the invention could also be used for identifying other types of substances, for example, in situ characterization of composition of bore-hole walls, and in situ characterization of polymer and elastomer products and coatings.

Many other implementations of the invention, including additional variations and applications thereof, will be apparent to those skilled in the art.

References

1. Surowiex, A. J. et al., 1988, Dielectric Properties of Breast Carcinoma and the Surrounding Tissues, IEEE Trans. Biomed. Eng. 35(4):257–262.
2. Heintz, J. & O. Minet, 1995 Dielectric Properties of Female Breast Tumors, In Ninth International Conference on Electrical Bio-Impedance, Heidelberg.
3. Liefn, D. et al., 1998 Clinical Study on Electrical Impedance Method Used Diagnosis of Breast Diasi. In Tenth International Conference on Electrical Bio-Impedance. Barcelona.
4. Morimoto, et al., Measurement of Electrical Bio-Impedance of Breast Tumors, Eu. Serg. Res. 2292:86–92, 1990.
5. Dexter, G. et al, "In-Vivo Measurement of Tumor Conductiveness With Magnetic Bioimpedance Method", IEEE Trans Biomedical Engine", Vol. 47 No. 10 October 2000.
6. Prthig, R., (1978), Dielectric and Electronic Properties of Biological Materials, John Wiley, New York.
7. Schanna, O. F. et al., (1978), Impedance Measurement in Biological Cell. John Wiley, New York.
8. H. P. Schwan, Mechanisms Responsible for Electrical Properties of Tissue and Cell Suspensions, Med. Prog. Tech. 19:163–165, 1993.
9. Fricke, H. The Theory of Electrolytic Polarization. Philosophical Magazine 1932; (97):310–318.
10. Cole K S (1972) Membranes, Ions (1978) and Impulses. University of California Press, Berkeley.

What is claimed is:

1. A method of examining a substance volume to characterize its type, comprising:
    applying locally a polarizing magnetic field through the examined substance volume:
    applying RF pulses locally to said examined substance volume such as to invoke electrical response signals corresponding to the electrical impedance (EI) of the examined substance volume, and magnetic resonance (MR) response signals corresponding to the MR properties of the examined substance volume;
    detecting locally said EI and MR response signals; and
    utilizing said detected response signals for characterizing the type of substance in the examined substance volume based on said electrical impedance and said magnetic resonance properties of the examined substance.

2. The method according to claim 1, wherein said polarizing magnetic field is varied such as to vary the EI response signals and the MR response signals invoked from the examined substance volume, said variations in the response signals also being detected and utilized in characterizing the examined substance volume type.

3. The method according to claim 1, wherein said detected EI response signals invoked by the RF pulses are processed to calculate the effective electrical impedance of the examined substance volume, which calculated electrical impedance is utilized in characterizing the examined substance volume type.

4. The method according to claim 1, wherein said RF pulses invoke MR free induction decay (FID) signals, corresponding to the echos from excited spins in the examined substance volume when returning to equilibrium, which FID signals are detected and utilized in characterizing the examined substance volume type.

5. The method according to claim 1, wherein said RF pulses are applied locally via a transmission line in contact with one side of the examined substance, said RF pulses invoking reflected pulses which are detected and utilized in characterizing the examined substance volume type.

6. The method according to claim 1, further comprising detecting RF pulses transmitted through said examined substance volume, using a second transmission line being in contact with another side of the examined substance, and utilizing said transmitted RF pulses in characterizing the examined substance volume type.

7. The method according to claim 1, wherein said detected response signals are utilized to characterize the examined substance volume type by:
analyzing said detected response signals for predetermined parameters characterizing the examined substance volume type;
and comparing said predetermined parameters with corresponding parameters of known substance types to produce a best match.

8. The method according to claim 1, wherein said RF pulses are applied as a sequence of pulses in which some pulses are optimized for EI measurements, and others are optimized for MR measurements.

9. The method according to claim 1, wherein said detected MR response signals are analyzed for spin density, longitudinal relaxation time (T1), and/or transverse relaxation time (T2) of the examined substance volume.

10. The method according to claim 1, wherein said detecting of the EI and MR response signals includes:
collecting the EI response signals and the MR response signals;
analyzing said collected response signals for predetermined parameters characterizing the volume substance volume type;
modeling the signal parameters into a set of parameters; and
classifying said set of parameters according to known parameter sets of known substance types.

11. The method according to claim 1, wherein said invoked and detected magnetic resonance (MR) response signals are nuclear magnetic resonance (NMR) response signals.

12. The method according to claim 11, wherein said NMR response signals are enhanced by the prior injection of a contrast agent.

13. The method according to claim 1, wherein said invoked and detected magnetic resonance (MR) response signals are electron magnetic resonance (EMR) response signals.

14. The method according to claim 13, wherein said EMR response signals are enhanced by the prior injection of a contrast agent.

15. The method according to claim 1, wherein said examined substance volume is tissue examined to characterize it as cancerous or non-cancerous tissue.

16. The method of claim 1, wherein said applying locally said polarizing magnetic field and said applying locally said RF pulses is effected by a single probe.

17. The method of claim 16, wherein said detecting locally said EI and MR response signals is effected by said single probe.

18. Apparatus for examining a substance volume to characterize its type, comprising:
a probe, having a transmission line and means for applying locally a polarizing magnetic field through the examined substance volume;
and an electrical control and processing system for:
applying RF pulses locally via said transmission line to said examined substance volume such as to invoke reflection of electrical impedance (EI) response signals corresponding to the electrical impedance of the examined substance volume, and magnetic resonance (MR) response signals corresponding to the MR properties of the examined substance volume;
detecting locally, via said transmission line, said EI and MR response signals; and
utilizing said detected response signals for characterizing the examined substance volume type based on said electrical impedance and said magnetic resonance properties of the examined substance.

19. The apparatus according to claim 18, wherein said electrical control and processing system also: controls said means to vary the polarizing magnetic field such as to vary the EI response signals and MR response signals invoked from the examined substance; detects said variations in the response signals; and utilizes said detected variations in the response signals in characterizing the examined substance volume type.

20. The apparatus according to claim 18, wherein said electrical control and processing system processes the detected EI response signals invoked by the RF pulses to calculate the effective electrical impedance of the examined substance volume, and utilizes said calculated electrical impedance in characterizing the examined substance volume type.

21. The apparatus according to claim 18, wherein said electrical control and processing system applies RF pulses capable of invoking MR free induction decay (FID) signals, corresponding to the echos from excited spins in the examined substance volume when returning to equilibrium, detects said FID signals, and utilizes said detected FID signals in characterizing the examined substance volume type.

22. The apparatus according to claim 18, wherein said transmission line which is ended at one end by: an open end, a dipole, a V-shaped antenna, a conical antenna, a surface coil or a single-sided leaky end.

23. The apparatus according to claim 22, wherein said transmission line is ended at said one end by an open cavity.

24. The apparatus according to claim 22, wherein said one end of the transmission line is electrically connected to a tuning circuit permitting the impedance of said one end to be varied and thereby to vary the reflectivity of the transmission line.

25. The apparatus according to claim 24, wherein said tuning circuit also permits the strength of the magnetic field generated by the RF pulses to be varied.

26. The apparatus according to claim 22, wherein said probe further comprises at least one coil at said one end of the transmission line, said coil being oriented orthogonally to the transmission line axis so as to detect MR signals in the direction of the transmission line axis.

27. The apparatus according to claim 22, wherein said one end of the transmission line includes:
an inner conductive strip extending parallel to the longitudinal axis of the transmission line, and a pair of outer conductive strips, electrically connected to each other, extending parallel to, and on opposite sides of, said inner conductive strip, and separated therefrom by insulation;

a first RF coil located between said inner conductive strip and one of said outer conductive strips and extending perpendicularly to the longitudinal axis of the transmission line;

and a second RF coil located between said inner conductive strip and the other of said outer conductive strips and extending perpendicularly to the longitudinal axis of the transmission line.

28. The apparatus according to claim 22, wherein said one end of the transmission line includes:
  a first conductive strip extending parallel to the longitudinal axis of the transmission line;
  a second conductive strip extending parallel to said first conductive strip and separated therefrom by insulation;
  and an RF coil located between said first and second conductive strips and extending perpendicularly to the longitudinal axis of the transmission line.

29. The apparatus according to claim 18, wherein said means for applying locally a polarizing magnetic field is controllable by said electrical control and processing system to vary the polarizing magnetic field through the examined substance volume with respect to amplitude andlor depth.

30. The apparatus according to claim 29, wherein said means includes a permanent magnet movably mounted on said transmission line to vary the polarizing magnetic field through the examined substance volume with respect to amplitude and/or depth.

31. The apparatus according to claim 30, wherein said permanent magnet is movably mounted by means of an air cylinder carried by said transmission line.

32. The apparatus according to claim 18, wherein said means includes one or more electromagnetic coils movably mounted with respect to said transmission line to vary the polarizing magnetic field through the examined substance volume with respect to amplitude and/or depth.

33. The apparatus according to claim 18, wherein said means includes one or more electromagnetic coils carried by said transmission line and controllable by said electrical control and processing system to vary the polarizing magnetic field through the examined substance volume with respect to amplitude and/or depth.

34. The apparatus according to claim 18, wherein said means includes one or more electromagnetic coils surrounding a paramagnetic core carried by said transmission line and controllable by said electrical control and processing system to vary the polarizing magnetic field through the examined substance volume with respect to amplitude and/or depth.

35. The apparatus according to claim 18, wherein said apparatus further comprises
  a second transmission lines to be brought into contact with another sides of the examined substance such that RF pulses transmitted from one of said transmission lines and said second transmission line are transmitted through said examined substance volume and are detected by the other of said transmission lines;
  said electrical control and processing system utilizing said detected RF pulses in characterizing the examined substance volume type.

36. The apparatus according to claim 18, wherein said electrical control and processing system utilizes said detected response signals to characterize the examined substance volume type by:
  analyzing said response signals for predetermined parameters characterizing the examined substance volume type;
  and comparing said predetermined parameters with corresponding parameters of known substance types to produce a best match.

37. The apparatus according to claim 18, wherein said electrical control and processing system applies said RF pulses as a sequence of pulses in which some pulses are optimized for EI measurements, and others are optimized for MR measurements.

38. The apparatus according to claim 18, wherein said electrical control and processing system analyzes the detected MR response signals for spin density, longitudinal relaxation time (T1), and/or transverse relaxation time (T2) of the examined substance volume.

39. The apparatus according to claim 18, wherein said electrical control and processing system detects and processes said EI and MR response signals by:
  (One) collecting the EI response signals and the MR response signals;
  (Two) analyzing said collected response signals for predetermined parameters characterizing the examined substance volume type;
  (Three) modeling the signal parameters into a set of parameters; and
  (Four) classifying said set of parameters according to known parameter sets of known substance types.

40. The apparatus according to claim 18, wherein said electrical control and processing system utilizes the detected EI and MR response signals to characterize the examined tissue volume as cancerous or non-cancerous.

41. The apparatus according to claim 18, wherein said electrical control and processing system further includes an indicator for indicating the type of the examined substance volume as determined by said electrical control and processing system.

42. The apparatus according to claim 18, wherein the apparatus further comprises a marking device for marking the examined substance according to its type as determined by said electrical control and processing system.

43. The apparatus according to claim 18, wherein said probe further includes a current sensor for sensing the current passing through the examined substance volume.

44. The apparatus according to claim 18, wherein said probe includes an array of sensors.

45. The apparatus according to claim 18, wherein said probe is combined with a catheter.

46. The apparatus according to claim 18, wherein said probe is combined with a biopsy core needle.

47. The apparatus according to claim 18, wherein said probe is combined with a cutting tool.

48. The apparatus according to claim 18, wherein said invoked and detected magnetic resonance (MR) response signals are nuclear magnetic resonance (NMR) response signals.

49. The apparatus according to claim 18, wherein said invoked and detected magnetic resonance (MR) response signals are electron magnetic resonance (EMR) response signals.

50. A method of examining a substance volume to characterize its type, comprising:
  applying locally a polarizing magnetic field through the examined substance volume;
  applying RF pulses locally to said examined substance volume such as to invoke electrical response signals corresponding to the electrical impedance (EI) of the examined substance volume, and magnetic resonance (MR) response signals corresponding to the MR properties of the examined substance volume;

varying said polarizing magnetic field such as to vary said EI and MR response signals;

detecting locally said EI and MR response signals including said variations of said EI and MR response signals; and utilizing said detected response signals and said variations for characterizing the type of substance in the examined substance volume based on said electrical impedance and said magnetic resonance properties of the examined substance.

51. Apparatus for examining a substance volume to characterize its type, comprising:

means for applying locally a polarizing magnetic field through the examined substance volume;

a probe;

and an electrical control and processing system for:

applying RF pulses locally via said probe to said examined substance volume such as to invoke electrical impedance (EI) response signals corresponding to the electrical impedance of the examined substance volume, and magnetic resonance (MR) response signals corresponding to the MR properties of the examined substance volume;

varying said polarizing magnetic field such as to vary said EI and MR response signals;

detecting locally said EI and MR response signals including said variations of said EI and MR response signals; and utilizing said detected response signals and said variations for characterizing the type of substance in the examined substance volume based on said electrical impedance and said magnetic resonance properties of the examined substance.

* * * * *